United States Patent [19]
Hornback et al.

[11] Patent Number: 6,096,917
[45] Date of Patent: *Aug. 1, 2000

[54] ANTI-VIRAL COMPOUNDS

[75] Inventors: William J. Hornback, Fishers; Scott C. Mauldin; John E. Munroe, both of Indianapolis, all of Ind.

[73] Assignee: Eli Lilly and Company, Indianapolis, Ind.

[ * ] Notice: This patent is subject to a terminal disclaimer.

[21] Appl. No.: 09/214,534

[22] PCT Filed: May 2, 1997

[86] PCT No.: PCT/US97/07403

§ 371 Date: Jan. 6, 1999

§ 102(e) Date: Jan. 6, 1999

[87] PCT Pub. No.: WO97/42154

PCT Pub. Date: Nov. 13, 1997

Related U.S. Application Data

[60] Provisional application No. 60/016,925, May 6, 1996.

[51] Int. Cl.$^7$ ............................. C07C 249/02; C07C 249/04
[52] U.S. Cl. .............................. 560/43; 560/35; 562/440; 564/248; 564/251
[58] Field of Search ............................. 560/43, 35; 562/440; 564/248, 251

[56] References Cited

U.S. PATENT DOCUMENTS

| | | |
|---|---|---|
| 2,703,809 | 3/1955 | Ritchie . |
| 2,744,100 | 5/1956 | Subluskey . |
| 2,744,102 | 5/1956 | Subluskey . |
| 2,750,382 | 12/1956 | Bible et al. . |
| 2,750,405 | 6/1956 | Ritchie et al. . |
| 2,750,407 | 6/1956 | Ritchie . |
| 2,753,357 | 7/1956 | Bible et al. . |
| 2,759,014 | 8/1956 | Bible . |
| 2,767,162 | 10/1956 | Picha . |
| 2,854,474 | 9/1958 | Bible . |
| 2,862,955 | 12/1958 | Hoehn . |
| 2,947,778 | 8/1960 | Bible . |
| 3,014,957 | 12/1961 | Hoehn . |
| 3,038,930 | 6/1962 | Bible . |
| 3,668,223 | 6/1972 | Jones . |
| 4,252,804 | 2/1981 | Joullie et al. . |
| 4,333,941 | 6/1982 | Baratz et al. . |
| 5,015,644 | 5/1991 | Roth et al. . |
| 5,276,053 | 1/1994 | Johnson . |
| 5,321,044 | 6/1994 | Peters et al. . |

FOREIGN PATENT DOCUMENTS

| | | |
|---|---|---|
| 0 540 143 A2 | 8/1992 | European Pat. Off. . |
| 0 806 203 A2 | 5/1997 | European Pat. Off. . |
| WO 97 41822 A | 11/1997 | WIPO . |
| WO 97 41860 A | 11/1997 | WIPO . |
| WO 97 41861 A | 11/1997 | WIPO . |
| WO 97 42145 A | 11/1997 | WIPO . |
| WO 97 42155 A | 11/1997 | WIPO . |
| WO 97 42156 A | 11/1997 | WIPO . |

OTHER PUBLICATIONS

Ueda, et al.: "The Leaf Oil and Resin Acid Components of Lacebark Pine, Pinus bungeana Zucc." Tottori Daigaku Kogakubu Kenkyu Hokiku, vol. 20, No. 1, 1989 Japan, pp. 87–96.
CAPLUS Abstr., No. 74:112247, Turner, et al., J. Chem. Soc. C., 1971, vol. 3, 547–553.
CAPLUS Abstr., No. 81;169653, Cambie, et al., Aust. J. Chem., 1974, vol. 27, No. 9, 2001–2016.
CAPLUS Abstr., No. 85:177668, Tahara, et al., Chem. Pharm. Bull., 1976, vol. 24, No. 7, 1497–1501.
CAPLUS Abstr., No. 121;116357, Standley, et al., J. Atmos. Chem., 1994, vol. 18, No. 1, 1–15.
CAPLUS Abstr., No. 124:317517, Matsumoto, et al., Chem. Pharm. Bull., 1996, vol. 44, No. 3, 530–533.
CAPLUS Abstr., No. 99:212742, Burnell, et al., Can. J. Chem., 1983, vol. 61, No. 11, 2461–2465.
CAPLUS Abstr., No. 102:79171, Burnell, et al., Synth. Commun., 1984, vol. 14, No. 13, 1229–1237.
CAPLUS Abstr., No. 113;152784, Cambie, et al., Aust. J. Chem., 1990, vol. 43, No. 5, 883–893.
CAPLUS Abstr., No. 121;35902, Matsumoto, et al., Chem. Pharm. Bull., 1993, vol. 41, No. 11, 1960–1964.
Chemical Abstracts, Abstract #2502; vol. 50, No. 4, Feb. 25, 1956, Michitoshi Ohta.
G. Defaye–Duchateau, "Oxydations dans la serie de l'acide dehydroabietique," 1964, Paris, 1469–1473.
Georges Dupont, et al., "Oxydation de l'acide abietique par l'acetate mercurique.Derives de l'acide dehydroabietique substitutes dans le cycle B," 1955, Paris, 708–715.
J. C. Sircar, et al., "Free–Radical Bromination of Methyl Abietate by N–Bromosuccinimide and Solvolysis of the Products,", vol. 35, No. 9, Sep., 1970, 3090–3093.
Chem. Abstr., vol. 112, No. 21, May 21, 1990, Abstract No. 198830, Sugai, et al.
Chem. Abstr., vol. 110, No. 9, Feb. 27, 1989, Abstract No. 75825, Nishi, et al.
Chem. Abstr., vol. 91, No. 23, Dec. 3, 1979, Abstract No. 193454, Pelletier, et al.
Chem. Abstr., vol. 81, No. 7, Aug. 19, 1974, Abstract No. 25842, Wirthlin, et al.
Chem. Abstr., vol. 121, No. 17, Oct. 24, 1994, Abstract No. 195010, Tagat, et al.
Chem. Abstr., vol. 120, No. 11, Mar. 11, 1994, Abstract No. 134850, Selwood, et al.
Chem. Abstr., vol. 61, No. 5, Aug. 31, 1964, Abstract No. 5699f, Tahara, et al.

(List continued on next page.)

Primary Examiner—Jane Fan
Attorney, Agent, or Firm—Arlene K. Musser

[57] ABSTRACT

The present invention provides compounds which inhibit an envelope virus by inhibiting the fusion of the virus with the host cell. The virus may be inhibited in an infected cell, a cell susceptible of infection or a mammal in need thereof.

7 Claims, No Drawings

OTHER PUBLICATIONS

Helvetica Chemica Acta., vol. 57, No. 2, Mar. 13, 1974, Basel Ch., 351–368.

Tetrahedron, vol. 21, No. 8, Aug. 1965, Oxford GB, 2133–2154.

Database Crossfire, Beilstein Informationsysteme, GMBH. Frankfurt DE, Beilstein registry No. 5483432, XP002061126, Cruz Frederico G., et al., Phytochemistry, vol. 31, No. 8, 1992, pp. 2793–2796.

Chem. Abstr., vol. 110, No. 21, Nov. 20, 1989, Abstract No. 195166, Node, et al.

Chem. Abstr, vol. 88, No. 25, Jun. 19, 1978, Abstract No. 191065, Ichinohe.

Chem. Abstr., vol. 83, No. 11, Sep. 15, 1975, Abstract No. 97643, Ichinohe.

Chem. Abstr., vol. 81, No. 5, Aug. 5, 1974, Abstract No. 25842, Wirthlin, et al.

Database Crossfire, Beilstein Informationssysteme, GMBH. Frankfort DE, Beilstein registry No. 4824891, XP002060909, Richard C. Cambie, et al., Australian Journal of Chemistry, vol. 44, No. 11, 1991, pp. 1553–1573.

Database Crossfire, Beilstein Informationssysteme, GMBH. Frankfurt DE, Beilstein registry No. 2179057, XP002060813, Richard C. Cambie, et al., Australian Journal of Chemistry, vol. 27, 1974, pp. 2413–2419.

Database Crossfire, Beilstein Informationssysteme, GMBH. Frankfurt DE, Beilstein registry No. 2887142, XP002060814, Richard C. Cambie, et al., Australian Journal of Chemistry, vol. 25, 1972, pp. 974–980.

Database Crossfire, Beilstein Informationssysteme, GMBH. Frankfurt DE, Beilstein registry No. 2920097, XP00206015, Richard C. Cambie, et al., Australian Journal of Chemistry, vol. 27, 1994, pp. 2001–2011.

Comptes Rendus De l'acadamie Bulgare des sciences, vol. 48, No. 11–12, 1995.

ANTI-VIRAL COMPOUNDS

CROSS-REFERENCE

This application is a 371 of PCT/US97/07403 filed on May 2, 1997 which claims the benefit of U.S. Provisional Patent Application Ser. No. 60/016,925 filed May 6, 1996.

Influenza viruses cause an infectious disease for which there is no adequate therapeutic agent. The disadvantages of existing treatments include the onset of clinical resistance within thirty six hours and the ineffectiveness of the agents against influenza B. Killed influenza virus vaccines have been available for over sixty years. However, these vaccines have not lessened the morbidity, mortality or severe financial loss caused by this disease. It follows that an agent which treats or prevents an influenza infection or is effective at preventing the clinical symptoms associated with an influenza infection will result in a significant benefit to society.

Currently, the only compounds approved for the therapeutic and prophylactic treatment of influenza infections are the adamantanes: amantadine and rimantadine. These compounds inhibit influenza A by inhibiting the function of the M2 ion channel activity of the virus. Amantadine is a potent in vitro inhibitor of influenza A virus as demonstrated by standard antiviral assays such as the plaque reduction assay. Amantadine is effective in reducing the duration of fever and other systemic complaints including but not limited to myalgia (muscular ache) and fatigue when administered to individuals infected with influenza A within forty-eight hours of the onset of clinical symptoms. It has also been observed that amantadine results in a one hundred-fold decrease of virus titer in the nasal washes of human volunteers infected with wild-type influenza virus which correlates with a dramatic decrease in fever score. Thus, in vitro influenza inhibition is predictive of useful in vivo effects, i.e. a reduction of the clinical symptoms associated with the influenza infection.

The present invention derives from the fact that influenza is an enveloped virus which dictates that the virus envelope must be fused with the endosomal membrane of the host cell in order to initiate the process of introducing its genetic information into the cell. Because this process is common to all enveloped viruses, it is an attractive target for antiviral chemotherapy. Examples of envelope viruses which are inhibited according to the present invention include influenza, bovine diarrheal, hepatitis C, tick borne encephalitis and the like. The fusion domain of the envelope glycoprotein of influenza, hemagglutinin (HA) has been well-characterized. See, White J. M., Annu. Rev. Physiol. vol. 52, pages 675–697 (1990) which is herein incorporated by reference.

Influenza virus HA provides at least two distinct functions: 1) recognition of the host cell receptor, i.e., sialic acid residues on glycoconjugates, and 2) fusion of the viral envelope with the endosomal membrane. Both functions are essential for the propagation of influenza virus in vitro and in vivo. During viral maturation, monomeric HA is inserted into a lipid bilayer, post-translationally modified and oligomerized into a trimer of identical subunits (trimeric HA). The infectivity of the progeny virus is contingent upon a site-specific cleavage of HA by host cell protease(s). This cleavage results in the formation of two polypeptide chains, HA1 and HA2, which remain associated by non-covalent interactions as well as by an intermolecular and intramolecular disulfide bonds.

It has been established that influenza HA has two functionally relevant conformations. One conformation (Form A) exists as a metastable structure at neutral pH and mediates receptor recognition. Following receptor mediated binding to the host cell, the virus is transported to the endosomal compartment where it encounters an acidic environment. The low pH triggers a dramatic structural rearrangement of HA (Form A) which results in the formation of the other, more stable conformation of HA (Form B).

Form B of HA is required for fusion of the virus envelope with the endosomal membrane. It is the structural rearrangement from Form A to Form B of HA that allows the fusion domain of HA to directly interact with the endosomal membrane enabling the release of viral genetic information into the host cell cytoplasm. These considerations lend themselves to the development of a strategy for antiviral intervention based on the abrogation of HA-mediated fusion of virus-host membranes.

The present invention relates to a compound of the formula:

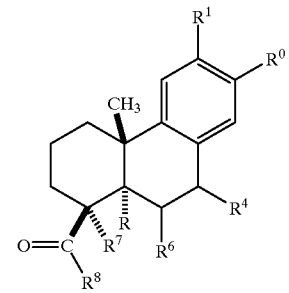

I wherein:

R is hydrogen;

$R^0$ and $R^1$ are independently hydrogen, hydroxy, $C_1$–$C_6$ alkyl, $C_1$–$C_6$ alkoxy, hydroxy($C_1$–$C_6$ alkyl), sulfhydryl, sulfamyl, —$SO_2$—Cl, —S—C(O)—N($CH_3$)$_2$, amino, $C_1$–$C_4$ alkylamino, di($C_1$–$C_4$ alkyl)amino, $C_1$–$C_4$ alkylsulfonylamino, di($C_1$–$C_4$ alkylsulfonyl)amino —$X^0$—O—C(O)—$C_1$–$C_4$ alkyl, —O—($X^1$)$_i$—$X^2$, —C(O)—$X^3$, —N—C(O)—$R^2$ or —O—$R^3$;

$X^0$ is a bond or divalent($C_1$–$C_6$ alkyl);

$X^1$ is an amino acid;

$X^2$ is hydrogen or an amino protecting group;

i is 1, 2 or 3;

$X^3$ is $C_1$–$C_6$ alkyl, $C_1$–$C_6$ alkoxy, halo($C_1$–$C_6$ alkyl), hydroxy($C_1$–$C_6$ alkyl) or phenyl;

$R^2$ is $C_1$–$C_4$ alkyl, $C_1$–$C_4$ alkoxy, halo($C_1$–$C_4$ alkyl), hydroxy($C_1$–$C_4$ alkyl), phenyl, p-methoxy-phenyl, p-fluoro-phenyl, naphthyl, pyridyl, piperidinyl, thiazolyl, oxazolyl, thienyl, furyl, tetrahydrofuryl or cyclohexyl;

$R^3$ is $C_1$–$C_6$ alkenyl, —$CH_2$—$R^{3a}$, —C(O)—$R_{3b}$, —C(S)—$R_{3c}$, —C($CH_3$)$_2$C(O)$NH_2$, phenyl or a group of the formula:

$R_{3a}$ is phenyl, p-fluorophenyl, pyridyl, pyrrolidinyl, piperidinyl, piperazinyl, morpholinyl, N-($C_1$–$C_4$ alkoxycarbonyl)piperidinyl, N-(trifluoromethyl)-piperidinyl, thiazolyl, oxazolyl, imidazolyl, isothiazolyl, isooxazolyl, quinolyl, isoquinolyl, thienyl, furyl, tetrahydrothienyl, tetrahydrofuryl, cyclohexyl, cyclopentyl, cyclopropyl or naphthyl;

$R^{3b}$ is pyrrolidinyl, piperidinyl, piperazinyl, morpholinyl, N-($C_1$–$C_4$ alkoxycarbonyl)piperidinyl, N-(trifluoromethyl)piperidinyl benzyloxy, pyridylmethyloxy, $C_1$–$C_6$ alkoxy, halo($C_1$–$C_4$ alkoxy), amino, $C_1$–$C_4$ alkylamino or di ($C_1$–$C_4$ alkyl)amino;

$R^{3c}$ is amino, $C_1$–$C_4$ alkylamino or di($C_1$–$C_4$ alkyl)amino;

$R^{3d}$ is oxygen, hydroximino, hydrazino or =CHZ;

Z is hydrogen, $C_1$–$C_4$ alkyl, halogen, di($C_1$–$C_4$ alkyl) amino, $C_1$–$C_4$ alkoxycarbonyl, carbamoyl($C_1$–$C_4$ alkyl), N-($C_1$–$C_4$ alkyl)carbamoyl or N,N-di($C_1$–$C_4$ alkyl)carbamoyl;

$R^{3e}$ is hydrogen, nitro or trifluoromethyl;

X is a bond or —($CH_2$)—;

$R^4$ is hydrogen, hydroxy, amino, $C_1$–$C_4$ alkylamino, di($C_1$–$C_4$ alkyl)amino, $C_1$–$C_4$ alkoxy, =O, —O—S($CH_3$)$_2$C($CH_3$)$_3$, $C_2$–$C_6$ alkanoyloxy, N-($C_2$–$C_6$ alkanoyl)amino, =N—$R^5$ or $R^4$ and $R^6$ combine to form a bond;

$R^5$ is hydroxy, amino, $C_1$–$C_4$ alkylamino, di($C_1$–$C_4$ alkyl) amino, $C_1$–$C_4$ alkoxy, pyridylmethoxy, benzyloxy, piperazinyl, N-(methyl)piperazinyl or —O—$CH_2$—C(O)—$R^{5a}$;

$R^{5a}$ is hydroxy or $C_1$–$C_4$ alkoxy;

$R^6$ is hydrogen, halo, $C_1$–$C_4$ alkyl or =O;

$R^7$ is hydrogen or $C_1$–$C_4$ alkyl;

$R^8$ is hydroxy, halo, $C_1$–$C_6$ alkoxy, pyrrolidinyl, piperidinyl, piperazinyl, 4-methyl-piperazinyl, morpholinyl or —N($R^9$))—$R^{10}$;

$R^9$ is hydrogen or methyl;

$R^{10}$ is -(divalent $C_1$–$C_6$ alkyl)-$R^{10a}$;

$R^{10a}$ is pyridyl, with the proviso that i) when $R^4$ is hydrogen, hydroxy or =O; and $R^8$ is hydroxy or $C_1$–$C_6$ alkoxy; then $R^0$ cannot be $C_1$–$C_6$ alkyl;

ii) when $R^8$ is $C_1$–$C_6$ alkoxy; and $R^4$ is hydrogen or =O; then $R^1$ cannot be hydroxy or methoxy;

or a pharmaceutically acceptable salt thereof.

The present invention provides new compounds of formula I, as described above, that are useful for treating or preventing a viral infection where the virus is an envelope virus that undergoes hemagglutinin-mediated fusion with a host cell and/or the resultant symptoms. These compounds, their pharmaceutically acceptable salts and the corresponding pharmaceutical formulations can be used alone or in combination with other antivirals, immunomodulators, antibiotics or vaccines.

All temperatures stated herein are in degrees Celsius (° C.). All units of measurement employed herein are in weight units except for liquids which are in volume units.

The term "halo" represents chloro, fluoro, bromo or iodo.

The term "$C_1$–$C_6$ alkyl" represents a straight or branched alkyl chain having from one to six carbon atoms. Typical $C_1$–$C_6$ alkyl groups include methyl, ethyl, propyl, isopropyl, butyl, isobutyl, sec-butyl, t-butyl and the like. The term "$C_1$–$C_6$ alkyl" includes within its definition the term "$C_1$–$C_4$ alkyl."

The term "halo($C_1$–$C_6$)alkyl" represents a straight or branched alkyl chain having from one to six carbon atoms with 1, 2 or 3 halogen atoms attached to it. Typical halo ($C_1$–$C_6$)alkyl groups include chloromethyl, 2-bromoethyl, 1-chloroisopropyl, 3-fluoropropyl, 2,3-dibromobutyl, 3-chloroisobutyl, iodo-t-butyl, trifluoromethyl and the like.

The term "hydroxy($C_1$–$C_6$)alkyl" represents a straight or branched alkyl chain having from one to six carbon atoms with an hydroxy group attached to it. Typical hydroxy ($C_1$–$C_6$)alkyl groups include hydroxymethyl, 2-hydroxyethyl, 1-hydroxyisopropyl, 2-hydroxypropyl, 2-hydroxybutyl, 3-hydroxyisobutyl, hydroxy-t-butyl, hydroxypentyl and the like.

The term "$C_1$–$C_4$ alkylamino" represents a straight or branched alkylamino chain having from one to four carbon atoms attached to an amino group. Typical $C_1$–$C_4$ alkylamino groups include methylamino, ethylamino, propylamino, isopropylamino, butylamino, sec-butylamino and the like.

The term "di($C_1$–$C_4$)alkylamino" represents a straight or branched dialkylamino chain having two alkyl chains, each having independently from one to four carbon atoms attached to a common amino group. Typical di($C_1$–$C_4$) alkylamino groups include dimethylamino, ethylmethylamino, methylisopropyl-amino, t-butylisopropylamino, di-t-butylaminno and the like.

The term "$C_1$–$C_6$ alkoxy" represents a straight or branched alkyl chain having from one to six carbon atoms attached to an oxygen atom. Typical $C_1$–$C_6$ alkoxy groups include methoxy, ethoxy, propoxy, isopropoxy, butoxy, t-butoxy, pentoxy and the like. The term "$C_1$–$C_6$ alkoxy" includes within its definition the term "$C_1$–$C_4$ alkoxy".

The term "$C_2$–$C_6$ alkenyl" represents a straight or branched alkenyl chain having from two to six carbon atoms. Typical $C_2$–$C_6$ alkenyl groups include ethenyl, propenyl, isopropenyl, buten-2-yl, t-butenyl, penten-1-yl, hexen-3-yl, 3-methylpentenyl and the like.

The term "$C_1$–$C_4$ alkoxycarbonyl" represents a straight or branched alkoxy chain having from one to four carbon atoms attached to a carbonyl moiety. Typical $C_1$–$C_4$ alkoxycarbonyl groups include methoxycarbonyl, ethoxycarbonyl, propoxycarbonyl, isopropoxycarbonyl, butoxycarbonyl, t-butoxycarbonyl and the like.

The term "carbamoyl($C_1$–$C_4$)alkyl" represents a straight or branched alkyl chain having from one to four carbon atoms with a carbamoyl group attached to it. Typical carbamoyl($C_1$–$C_4$)alkyl groups include carbamoylmethyl, carbamoylethyl, carbamoylpropyl, carbamoylisopropyl, carbamoylbutyl and carbamoyl-t-butyl and the like.

The term "N-($C_1$–$C_4$)alkylcarbamoyl" represents a straight or branched alkyl chain having from one to four carbon atoms attached to the nitrogen atom of a carbamoyl moiety. Typical N-($C_1$–$C_4$ alkyl)carbamoyl groups include N-methylcarbamoyl, N-ethylcarbamoyl, N-propylcarbamoyl, N-isopropylcarbamoyl, N-butylcarbamoyl, N-t-butylcarbamoyl and the like.

The term "N,N-di($C_1$–$C_4$ alkyl)carbamoyl" represents a straight or branched alkyl chain having a straight or branched $C_1$–$C_4$ alkyl chain attached to each of the nitrogen atoms on a carbamoyl moiety. Typical N-($C_1$–$C_4$)

alkylcarbamoyl groups include N,N-dimethylcarbamoyl, N-ethyl-N-methylcarbamoyl, N-propyl-N-butylcarbamoyl, N,N-diisopropylcarbamoyl, N-methyl-N-butylcarbamoyl and the like.

The term "$C_1$–$C_4$ alkylsulfonylamino" represents a straight or branched alkyl group having from one to four carbon atoms attached to a sulfonylamino moiety. Typical $C_1$–$C_4$ alkylsulfonylamino groups include methylsulfonylamino, ethylsulfonylamino, propylsulfonylamino, isopropyl-sulfonylamino, butylsulfonylamino, isobutylsulfonylamino, sec-butylsulfonylamino, and t-butylsulfonylamino.

The term "di($C_1$–$C_4$ alkylsulfonyl)amino" represents two $C_1$–$C_4$ alkylsulfonyl moieties attached to an amino moiety. Typical $C_1$–$C_4$ alkylsulfonylamino groups include methylsulfcnylamino, ethylsulfonylaminc, propylsulfonylamino, isopropylsulfonylamino, butylsulfonylamino, isobutylsulfonylamino, sec-butylsulfonylamino and t-butylsulfonylamino.

The term "$C_2$–$C_6$ alkanoyl" represents a straight or branched alkyl chain having from one to five carbon atoms attached to a carbonyl moiety. Typical $C_2$–$C_6$ alkanoyl groups include ethanol, propanoyl, isopropanoyl, butanoyl, t-butanoyl, pentanoyl, hexanoyl, 3-methylpentanoyl and the like.

The term "$C_2$–$C_6$ alkanoyloxy" represents a straight or branched alkyl group having from one to five carbon atoms attached to a carbonyloxy moiety. Typical $C_2$–$C_6$ alkanoyloxy groups include ethanoyloxy, propanoyloxy, isopropanoyloxy, butanoyloxy, isobutanoyloxy, sec-butanoyloxy, t-butanoyloxy, pentanoyloxy and the like.

The term "$C_2$–$C_6$ alkanoylamino" represents a straight or branched alkyl group one to five carbon atoms attached to a carbonylamino moiety. Typical $C_2$–$C_6$ alkanoylamino groups include ethanoylamino, propanoylamino, isopropanoyl-amino, butanoylamino, isobutanoylamino, sec-butanoylamino, t-butanoylamino, pentanoylamino and the like.

As mentioned above, the invention includes the pharmaceutically acceptable salts of the compounds defined by formula I. Although generally neutral, a compound of this invention can possess a sufficiently acidic, a sufficiently basic, or both functional groups, and accordingly react with any of a number of inorganic bases, and inorganic and organic acids, to form a pharmaceutically acceptable salt.

The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a mineral or organic acid or an inorganic base. Such salts are known as acid addition and base addition salts.

Acids commonly employed to form acid addition salts are inorganic acids such as hydrochloric acid, hydrobromic acid, hydroiodic acid, sulfuric acid, phosphoric acid and the like, and organic acids such as p-toluenesulfonic, methanesulfonic acid, oxalic acid, p-bromophenylsulfonic acid, carbonic acid, succinic acid, citric acid, benzoic acid, acetic acid, and the like.

Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, γ-hydroxybutyrate, glycollate, tartrate, methanesulfonate, propanesulfonate, naphthalene-1-sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is not of a critical nature, so long as the salt as a whole is pharmacologically acceptable and as long as the counterion does not contribute undesired qualities to the salt as a whole.

The term "amino-protecting group" as used in the specification refers to substituents of the amino group commonly employed to block or protect the amino functionality while reacting other functional groups on the compound. Examples of such amino-protecting groups include formyl, trityl, phthalimido, trichloroacetyl, chloroacetyl, bromoacetyl, iodoacetyl groups, or urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, t-butoxycarbonyl, 2-(4-xenyl) isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl)-prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)-ethoxycarbonyl, 2-(methylsulfonyl)ethoxycarbonyl, 2-(triphenylphosphino)-ethoxycarbonyl, fluorenylmethoxycarbonyl ("FMOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy) benzyloxycarbonyl, isobornyloxycarbonyl, 1-piperidyloxycarbonyl and the like; benzoylmethylsulfonyl, 2-nitrophenylsulfenyl, diphenylphosphine oxide and like amino-protecting groups. The species of amino-protecting group employed is not critical so long as the derivatized amino group is stable to the condition of subsequent reaction(s) on other positions of the intermediate molecule and can be selectively removed at the appropriate point without disrupting the remainder of the molecule including any other amino-protecting group(s).

Preferred amino-protecting groups are t-butoxycarbonyl (t-Boc), allyloxycarbonyl and benzyloxycarbonyl (CbZ). Further examples of groups referred to by the above terms are described by J. W. Barton, "Protective Groups in Organic Chemistry", J. G. W. McOmie, Ed., Plenum Press, New York, N.Y., 1973, Chapter 2, and T. W. Greene, "Protective Groups in Organic Synthesis", John Wiley and sons, New York, N.Y., 1981, Chapter 7.

The term "carboxy-protecting group" as used in the specification refers to substituents of the carboxy group commonly employed to block or protect the carboxy functionality while reacting other functional groups on the compound. Examples of such carboxy-protecting groups include methyl, p-nitrobenzyl, p-methylbenzyl, p-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxy-benzhydryl, 2,2',4,4'-tetramethoxybenzhydryl, t-butyl, t-amyl, trityl, 4-methoxytrityl, 4,4'-dimethoxytrityl, 4,4',4"-trimethoxytrityl, 2-phenylprop-2-yl, trimethylsilyl, t-butyldimethylsilyl, phenacyl, 2,2,2-trichloroethyl, β-(dibutylmethylsilyl)ethyl, p-toluenesulfonylethyl, 4-nitrobenzylsulfonylethyl, allyl, cinnamyl, 1-(trimethylsilylmethyl)prop-1-en-3-yl and like moieties. Preferred carboxy-protecting groups are allyl, benzyl and t-butyl. Further examples of these groups are found in E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5.

Preferred compounds are those compounds of formula I where:

$R^0$ is hydrogen, hydroxy, $C_1$–$C_6$ alkyl, $C_1$–$C_6$ alkoxy, hydroxy($C_1$–$C_6$ alkyl), —$X^0$—O—C(O)—$C_1$–$C_4$ alkyl, —O—($X^1$)$_i$—$X^2$, —C(O)—$X^3$ or —O—$R^3$;

$R^1$ is hydrogen, hydroxy, $C_1$–$C_6$ alkoxy, sulfhydryl, sulfamyl, —$SO_2$—Cl, amino, di($C_1$–$C_4$ alkylsulfonyl)amino —C(O)—$X^3$, —N—C(O)—$R^2$ or —O—$R^3$;

$X^0$ is a bond or divalent($C_1$–$C_6$ alkyl);

$X^1$ is an amino acid;

$X^2$ is hydrogen or an amino protecting group;

i is 1 or 2;

$X^3$ is $C_1$–$C_6$ alkyl;

$R^2$ is hydroxy($C_1$–$C_4$ alkyl);

$R^3$ is $C_1$–$C_6$ alkenyl, —$CH_2$—$R^{3a}$, —C(O)—$R^{3b}$, —C(S)—$R^{3c}$, —C($CH_3$)$_2$C(O)$NH_2$ or a group of the formula:

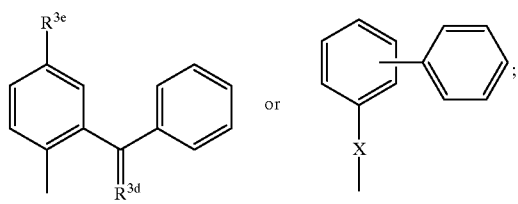

$R^{3a}$ is phenyl, p-fluorophenyl, pyridyl, piperidinyl, piperazinyl or morpholinyl;

$R^{3b}$ is piperidinyl, piperazinyl, morpholinyl, N-($C_1$–$C_4$ alkoxyoarbonyl)piperidinyl, N-(trifluoromethyl) piperidinyl, halo($C_1$–$C_4$ alkoxy) or di($C_1$–$C_4$ alkyl)amino;

$R^{3c}$ is di($C_1$–$C_4$ alkyl)amino;

$R^{3d}$ is oxygen or hydroximino;

$R^{3e}$ is hydrogen, nitro or trifluoromethyl;

X is a bond;

$R^4$ is hydrogen, hydroxy, amino, =O, $C_2$–$C_6$ alkanoyloxy, =N—$R^5$, —OSi($CH_3$)$_2$ or $R^4$ and $R^6$ combine to form a bond;

$R^5$ is hydroxy, amino, di($C_1$–$C_4$ alkyl)amino, $C_1$–$C_4$ alkoxy, pyridylmethoxy, N-(methyl)piperazinyl or —O—$CH_2$—C(O)—$R^{5a}$;

$R^6$ is hydrogen, chloro, bromo, methyl or =O;

$R^7$ is hydrogen or methyl;

$R^8$ is hydroxy, chloro, methoxy, 4-methylpiperazinyl or —N($R^9$)—$R^{10}$;

$R^9$ is hydrogen;

$R^{10}$ is —$CH_2$—$R^{10a}$; and $R^{10a}$ is pyridyl;

or a pharmaceutically acceptable salt thereof.

Of these compounds, more preferred are those compounds of formula I where:

$R^0$ is hydrogen, hydroxy, $C_1$–$C_6$ alkoxy, —O—($X^1$)$_i$—$X^2$, —$X^0$—O—C(O)—$C_1$–$C_4$ alkyl or —O—$R^3$;

$R^1$ is hydrogen, hydroxy, $C_1$–$C_6$ alkoxy or —O—$R^3$;

$X^0$ is a bond;

$X^1$ is an amino acid;

$X^2$ is hydrogen or an amino protecting group;

i is 1 or 2;

$R^3$ is $C_1$–$C_6$ alkenyl, —$CH_2$—$R^{3a}$ or —C(O)—$R^{3b}$;

$R^{3a}$ is p-fluorophenyl or pyridyl;

$R^{3b}$ is piperidinyl;

$R^4$ is hydrogen, hydroxy, =O or =N—$R^5$;

$R^5$ is hydroxy, dimethylamino or N-(methyl)piperazinyl;

$R^6$ is hydrogen, bromo or =O;

$R^7$ is methyl; and $R^8$ is methoxy;

or a pharmaceutically acceptable salt thereof.

Of these compounds, even more preferred are those compounds of formula I where:

$R^0$ is hydrogen, hydroxy, $C_1$–$C_4$ alkoxy, —O—($X^1$)$_1$—$X^2$, —O—C(O)methyl or —O—$R^3$;

$R^1$ is hydrogen, hydroxy, $C_1$–$C_4$ alkoxy or —O—$R^3$;

$X^1$ is glycine, alanine or valine;

$X^2$ is hydrogen, t-butoxycarbonyl or benzyloxycarbonyl;

$R^4$ is =O or =N—$R^5$;

$R^5$ is hydroxy;

$R^6$ is hydrogen;

or a pharmaceutically acceptable salt thereof.

The compounds of formula I may be prepared according to procedures known in the art. For example, the following Reaction Schemes may be used, alone or in combination to provide the desired compounds. Once a reaction is complete, the intermediate compound may be isolated by procedures well-known in the art, for example, the compound may be crystallized and then collected by filtration, or the reaction solvent may be removed by extraction, evaporation or decantation. The intermediate compound may be further purified, if desired, by common techniques such as crystallization or chromatography over solid supports such as silica gel or alumina, before carrying out the next step of the reaction scheme.

The compounds of formula I where $R^4$ is =O or =N—R may be prepared according to the procedures shown below in Reaction Scheme I.

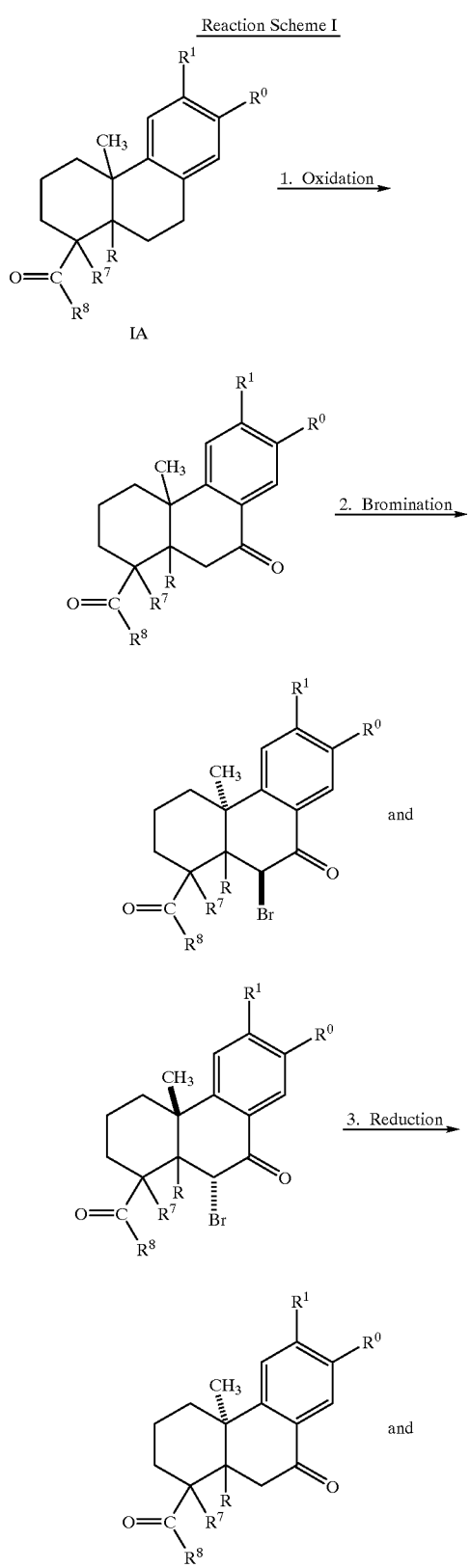

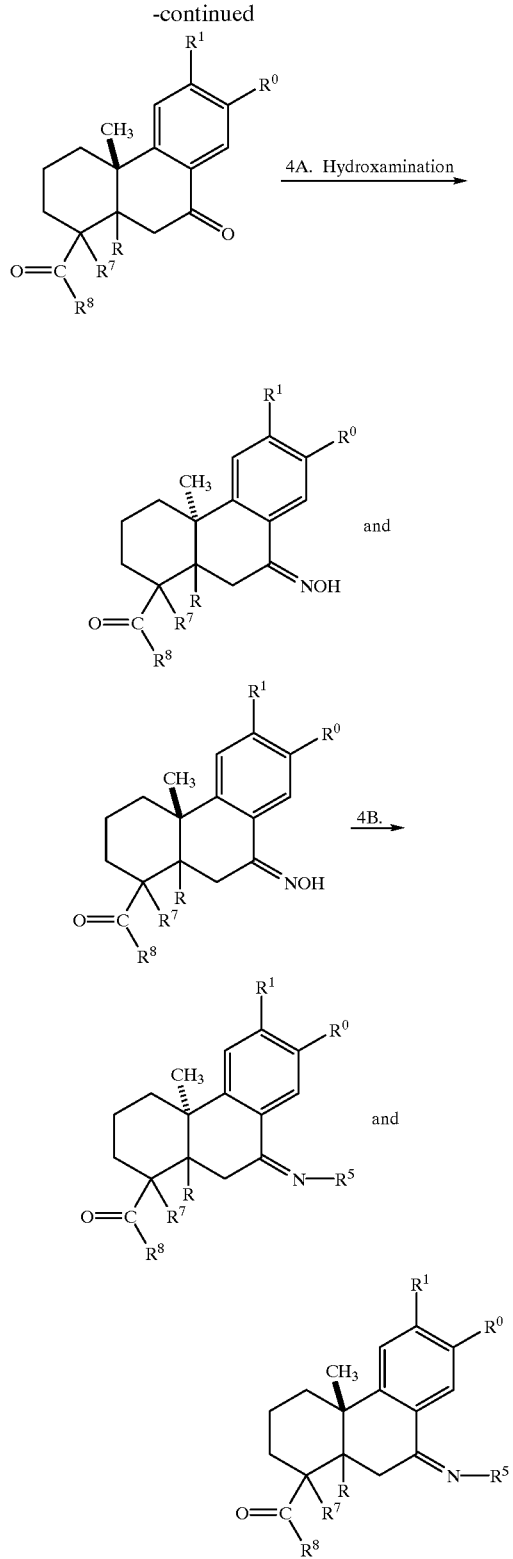

where Reactions I.4A and 4B represent alternative reactions that follow Reaction I.3.

Reaction scheme I is accomplished by carrying out reactions 1–4 is sequential order. Reaction I.1 is carried out by oxidizing a compound of formula IA, for example, by reaction with chromium trioxide in an acetic acid/water mixture, to provide the corresponding ketone. The chromium trioxide is generally employed in an amount ranging from equimolar proportions to about a 4 molar excess relative to the compound of formula IA, preferably in about a 2–4 molar excess. The acetic acid/water mixture is generally a 10:1 to a 2:1 mixture of acetic acid to water, preferably about 4:1. The reaction is generally substantially complete after about 1 to 10 hours when conducted at a temperature of from about 23° C. to about 60° C. The reaction is preferably conducted at a temperature of from about 23° C. to about 30° C. for about 5 to 10 hours.

In Reaction I.2, the ketone obtained from Reaction I.1 is reacted with bromine in a suitable solvent such as diethyl ether, tetrahydrofuran or dimethoxyethane, to provide a mixture of bromoketones which are then separated using standard separation techniques such as chromatography. These isomerically pure bromoketones are then used to prepare various isomerically pure compounds of formula I. The bromine is generally employed in an amount ranging from about equimolar proportions to about a 2 molar excess relative to the ketone reactant, preferably in about a 1–1.5 molar excess. Solvent choice is not critical so long as the solvent employed is inert to the ongoing reaction and the reactants are sufficiently solubilized to effect the desired reaction. The reaction is generally substantially complete after about 1 to 3 hours when conducted at a temperature of from about 23° C. to about 30° C. The reaction is preferably conducted at room temperature for about 1 to 1.5 hours.

Alternatively, the ketone obtained from Reaction I.1 is reacted with a silylating agent in the presence of a base in a suitable solvent such as methylene chloride, diethyl ether or tetrahydrofuran to provide the corresponding silylated enol ether. Preferred bases include 2,6-lutidine and collidine. A preferred silylating agent is t-butyldimethylsilyl trifluoromethanesulfonate. The silylating agent is generally employed in an amount ranging from about equimolar proportions to about a 2 molar excess relative to the ketone reactant, preferably in about a 1–1.5 molar excess. Solvent choice is not critical so long as the solvent employed is inert to the ongoing reaction and the reactants are sufficiently solubilized to effect the desired reaction. The reaction is generally substantially complete after about 30 minutes to 2 hours when conducted at a temperature of from about 0° C. to about 50° C. The reaction is preferably conducted at a temperature of from about 10° C. to about 25° C. for about 30 minutes to about 1 hour.

The silylated enol ether is then reacted with bromine substantially as described above with the exception that the reaction is carried out in the presence of acetic acid. Typical solvents suitable for use in this reaction include any organic solvent such as methylene chloride, diethyl ether or tetrahydrofuran. Solvent choice is not critical so long as the solvent employed is inert to the ongoing reaction and the reactants are sufficiently solubilized to effect the desired reaction.

In Reaction I.3, the bromoketone is reduced, for example by reaction with zinc dust and sodium acetate in glacial acetic acid, to provide the corresponding ketones. The zinc is generally employed in an amount ranging from about equimolar proportions to about a 4 molar excess relative to the ketone reactant, preferably in about a 1.5–3 molar excess. The sodium acetate is generally employed in an amount ranging from about 0.6 molar equivalents to about 1.2 molar equivalents relative to the ketone reactant. The reaction is generally substantially complete after about 1 to 10 hours when conducted at a temperature of from about 60° C. to the reflux temperature of the mixture. The reaction is preferably conducted at reflux temperature for about 1 to 2 hours.

Alternatively, hydroxylamine hydrochloride is reacted with sodium acetate in a suitable solvent such as ethanol. The sodium acetate is generally employed in an amount ranging from about 1.1 molar equivalents to about a 50 molar excess relative to the hydroxylamine. The reaction is generally substantially complete after about 1 to 72 hours when conducted at a temperature of from about 25° C. to about 80° C. The reaction is preferably conducted at a temperature in the range of from about 25° C. to about 30° C. for about 5 to 24 hours.

In Reaction I.4A, the ketone obtained from Reaction I.3 is reacted with hydroxylamine hydrochloride in a mixture of methanol, water and acetic acid to provide the desired oxime compound. The hydroxylamine hydrochloride is generally employed in an amount ranging from about equimolar proportions to about a 4 molar excess relative to the ketone reactant, preferably in about a 1.3–3 molar excess. The ratio of methanol to water to acetic acid is generally 10–20:1:0.1, preferably 15:1:0.1. The reaction is generally substantially complete after about 1 hour to about 2 days when conducted at a temperature of from about 40° C. to the reflux temperature of the mixture. The reaction is preferably conducted at reflux temperature for about 1 to 6 hours.

In Reaction I.4B, the ketone obtained from Reaction I.3 is reacted with an hydrazine hydrochloride such as 1-amino-4-methylpiperazine, 1,1-dimethylhydrazine or hydrazine in the presence of a base in an inert solvent at a temperature of from about 25° C. to 80° C. for 2 to 24 hours. Typical bases include sodium acetate, potassium hydroxide, triethylamine and the like. Suitable solvents include ethanol, isopropanol and dimethylformamide. Solvent choice is not critical so long as the solvent employed is inert to the ongoing reaction and the reactants are sufficiently solubilized to effect the desired reaction.

The phenyl moiety of the compounds of formula I prepared above may be substituted according to Reaction Scheme II, as follows.

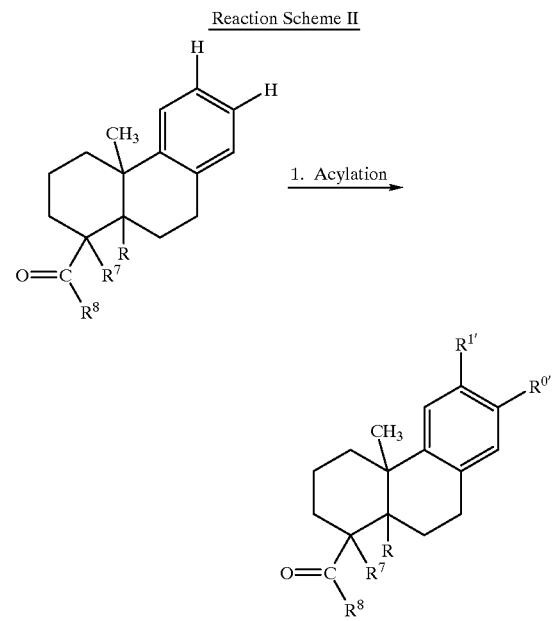

-continued

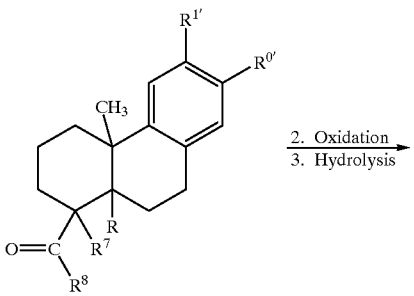

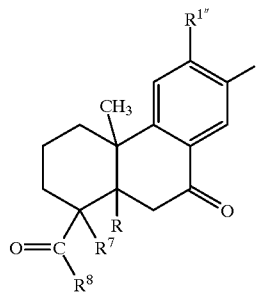

where $R^{0\prime}$ and $R^1$ are independently hydrogen or —C(O)CH$_3$; and $R^{0\prime\prime}$ and $R^{1\prime\prime}$ are independently hydrogen or hydroxy.

In Reaction II.1, the compound of formula I where $R^0$ and $R^1$ are each hydrogen is subjected to a Friedel-Crafts acylation by reacting the compound of formula I with an acid halide, in the presence of a catalyst in an inert solvent such as carbon disulfide. The acid halide is generally employed in an amount ranging from about equimolar proportions to about a 1.5 molar excess relative to the compound of formula I, preferably in about a 1.1–1.3 molar excess. Preferred acid halides include acetyl chloride, acetyl bromide or the like. Preferred catalysts include aluminum trichloride, aluminum tribromide or the like. Solvent choice is not critical so long as the solvent employed is inert to the ongoing reaction and the reactants are sufficiently solubilized to effect the desired reaction. The reaction is generally substantially complete after about 1 to 10 hours when conducted at a temperature of from about 50° C. to the reflux temperature of the mixture. The reaction is preferably conducted at reflux temperature for about 1 to 2 hours.

In Reaction II.2, the acylated compound of formula I obtained from Reaction II.1 is oxidized to provide the corresponding phenol in a two step reaction. First, the acyl moiety is reacted with a peracid in the presence of an acid catalyst in an inert solvent such as dimethoxyethane to provide the corresponding ester with is then reacted with sodium bicarbonate in an alcohol/water mixture to provide the desired phenol.

The peracid is generally employed in an amount ranging from about equimolar proportions to about a 2 molar excess relative to the acyl moiety, preferably in about a 1–1.3 molar excess. The amount of catalyst typically employed is in the range of 0.005–0.04 equivalents relative to the acyl moiety. A preferred peracid is metachloro-peroxybenzoic acid. A preferred catalyst is p-toluenesulfonic acid. Solvent choice is not critical so long as the solvent employed is inert to the ongoing reaction and the reactants are sufficiently solubilized to effect the desired reaction. The reaction is generally substantially complete after about 1 to 10 hours when conducted at a temperature of from about 50° C. to the reflux temperature of the mixture. The reaction is preferably conducted at reflux temperature for about 1 to 3 hours.

The resultant ester is typically refluxed with a base in a methanol/water mixture for about 1 to 7 hours to provide the desired phenol compound. Preferred bases include sodium bicarbonate, sodium carbonate, sodium hydroxide or potassium hydroxide or the like. The base is generally employed in an excess, for example from about a 1 molar excess to about a 6 molar excess relative to the ester moiety, preferably in about a 2–5 molar excess.

The phenol compounds obtained from Reaction Scheme II may be used to prepare various substituted compounds of formula I, as described below.

For example, the hydroxy moiety may be alkylated by reacting the phenol compound with a suitable alkylating agent in the presence of a base in an inert solvent. Examples of bases include triethylamine, diisopropyl ethylamine, sodium hydride and potassium carbonate. Typical solvents include methylene chloride, tetrahydrofuran, dimethylformamide and the like. Solvent choice is not critical so long as the solvent employed is inert to the ongoing reaction and the reactants are sufficiently solubilized to effect the desired reaction. Suitable alkylating agents include iodomethane, allyl iodide, p-fluorophenyl bromide, 3-bromomethyl-pyridine and 2-fluorobenzophenone and the like. The reaction is generally substantially complete after about 1 to 20 hours when conducted at a temperature of from about 0° C. to 170° C. The reaction is preferably conducted at a temperature of from about 25° C. to about 80° C. for about 4 to 16 hours.

Alternatively, the hydroxy moiety may be alkylated by reacting the phenol with an alcohol in the presence of triphenylphosphine and a suitable activating agent in an inert solvent, such as tetrahydrofuran or ethylene glycol dimethyl ether. Examples of suitable activating agents include diethyl azodicarboxylate, dimethyl azodicarboxylate, diisopropyl azodicarboxylate and the like. Examples of alcohols include 3-pyridyl carbinol, N-t-butoxycarbonyl-3-piperidinemethanol and the like. The reaction is generally substantially complete after about 0.5 to 2 hours when conducted at a temperature of from about 0° C. to 85° C. The reaction is preferably conducted at a temperature of from about 25° C. to about 70° C. for about 30 minutes to 1 hour.

The hydroxy moiety may be converted to an ester or a carbonate by reacting the phenol with an acylating agent in the presence of a base in an inert solvent, such as methylene chloride, tetrahydrofuran or dimethylformamide. Typical bases include triethylamine, diisopropyl ethylamine, sodium hydride and the like. Typical acylating agents include N-(t-butoxycarbonyl)-4-chlorocarbonyl piperdine, 2,2,2-trichloroethyl chloroformate, N-(t-butoxycarbonyl)-hydroxybenzotriazole amino esters. The reaction is generally substantially complete after about 1 to 20 hours when conducted at a temperature of from about 0° C. to 60° C. The reaction is preferably conducted at a temperature of from about 10° C. to about 25° C. for about 1 to 5 hours.

The hydroxy moiety may be converted to the corresponding aniline in a three step reaction. First, the phenol is reacted with a suitably substituted amide such as 2-methyl-2-bromo-propanamide in the presence of a base such as sodium hydride or triethylamine in an inert solvent, such as dioxane or tetrahydrofuran at a temperature of 25° C. to 100° C. to provide the corresponding amido-ether. This amido-ether is then reacted with sodium hydride in an inert solvent such as dimethylformamide, 1,3-dimethyl-3,4,5,6-tetrahydro-2(1H)-pyrimidone or a mixture thereof at temperatures ranging from 25° C. to 145° C. to provide the rearranged amido-alcohol. Finally, the amido-alcohol is reacted with an acid, such as hydrochloric acid in dioxane at 50° C. to 100° C. to provide the desired aniline.

The aniline may be converted to the corresponding sulfonamide by reacting the aniline with a sulfonyl chloride such as methanesulfonyl chloride or isopropylsulfonyl chloride in the presence of a base, such as triethylamine, diisopropyl ethylamine or sodium hydride at a temperature of from about 0° C. to 50° C. in an inert solvent, such as methylene chloride, tetrahydrofuran or dimethylformamide.

The hydroxy moiety may be converted to a thiophenol in a three step reaction. First the phenol is reacted with a thio-carbamoyl (for example dimethylthiocarbamoyl chloride) in the presence of a base in an suitable solvent, such as water or dimethylformamide at a temperature ranging from 25° C. to 50° C. for 1 to 3 hours to provide the oxo-thiocarbamate.

Typical bases include potassium hydroxide, triethylamine and the like. The oxo-thiocarbamate is converted to the corresponding thio-oxocarbamate compound by isolating and heating the neat solid to its melting point. Finally, the thio-oxocarbamate is reacted with a base, such as potassium hydroxide or sodium hydroxide in an alcoholic solvent, such as methanol or ethanol at a temperature of 20° C. to 80° C. for 20 minutes to 1 hour to provide the corresponding thiophenol.

The thiophenol may be converted to the corresponding sulfonamides by reacting the thiophenol with an oxidizing agent (for example, potassium nitrate) in an inert solvent such as acetonitrile, followed by the addition of a chlorinating agent (for example, sulfuryl chloride) at temperatures ranging from 0° C. to 25° C. to provide a mixture of sulfonyl chlorides which are separable using standard chromatographic techniques. These sulfonyl chlorides may be converted to the desired sulfonamides by reaction with an appropriately substituted amine such as ammonium hydroxide, methylamine, isopropylamine or benzylamine at a temperature of from about 0° C. to 40° C. in an inert solvent such tetrahydrofuran.

The hydroxy moiety may be converted to the corresponding amino esters by reacting the phenol with an amino protected amino acid in the presence of a coupling reagent and a catalyst in an inert solvent such as diethyl ether, tetrahydrofuran or methylene chloride. Preferred amino protecting groups include t-butoxycarbonyl or benzyloxycarbonyl. The amino reactant is generally employed in equimolar proportions to a slight excess (1.3 equivalents) relative to the phenol reactant in the presence of an equimolar quantity to a slight excess (1.5 equivalents) of the coupling reagent. Typical coupling agents include dicyclohexylcarbodiimide (DCC), 1-(3-dimethylaminopropyl)-3-ethylcarbodiimide, benzotriazol-1-yloxy-tris(dimethylamino)phosphonium hexafluorophosphate (BOP), N,N'-diethylcarbodiimide, carbonyldiumidazole, bis(2—oxo-3-oxazolidinyl) phosphinic chloride (BOP-Cl) or N-ethoxycarbonyl-2-ethoxy-1,2-dihydroquinoline (EEDQ) and the like. Preferred coupling agents include DCC and BOP. Typical catalysts include DMAP and 4-pyrrolopyridine. The reaction is substantially complete in 1 to 10 hours when carried out at a temperature of from about −30° C. to about 35° C., preferably from about 0° C. to about 25° C.

The starting materials used in the procedures detailed above may be obtained commercially or prepared according to procedures known in the art. For example, methyl O-methylpodocarpate having the following stereochemistry may be obtained from Aldrich Chemical Company:

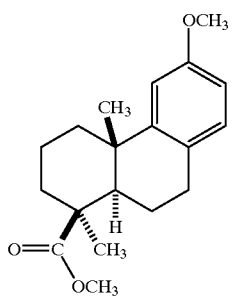

The following Preparations and Examples further illustrate specific aspects of the present invention. It is to be understood, however, that these examples are included for illustrative purposes only and are not intended to limit the scope of the invention in any respect and should not be so construed.

Preparation 1

N-t-Butoxycarbonyl-4-carboxy-piperidine

To a solution of 1.0 g (7.74 mmol) of 4-carboxy-piperidine in 40 ml of a 1:1 water/dioxane mixture, was added 3.2 g (23.2 mmol) of potassium carbonate ($K_2CO_3$) followed by 2.1 ml (9.3 mmol) of di(t-butyl)dicarbonate ($BOC_2O$). After 2 hours, the mixture was diluted with methylene chloride ($CH_2Cl_2$). The resulting layers were separated and the organic layer was dried over sodium sulfate ($Na_2SO_4$), filtered and concentrated in vacuo. The crude material was recrystallized from a 3:1 hot EtOAc/hexanes (EtOAc/hexanes) mixture.

Yield: 1.52 g (86%).

Preparation 2

N-t-Butoxycarbonyl-3-hydroxymethyl-piperidine

To a mixture of 5.0 g (43.4 mmol) of 3-hydroxymethyl-piperidine in 200 ml of $CH_2Cl_2$, was added 6.05 ml (43.4 mmol) of triethylamine ($Et_3N$), followed by 9.8 ml (43.4 mmol) of ($BOC_2O$). The reaction mixture was stirred for 1 hour at room temperature and then washed with 75 ml of a 0.1N hydrochloric acid solution (HCl), dried over $Na_2SO_4$, filtered and then concentrated in vacuo.

Yield: 7.1 g (76%).

Preparation 3

2-Bromo-2-methyl—propanamide

To a cold (0° C.) solution of 11 ml (89 mmol) of 2-bromo-2-methyl-propionyl bromide in 25 ml of hexane, was added 24 ml of concentrated ammonium hydroxide ($NH_4OH$), slowly. The reaction mixture was stirred for 20 minutes resulting in the formation of a white precipitate. This precipitate was isolated by filtration, washed 3 times with water ($H_2O$) and then dried in vacuo to provide 9.1 g of a white solid which was redissolved in 600 ml of hot chloroform ($CHCl_3$) and filtered immediately. The filtrate was combined with 2100 ml of hexane and cooled overnight.

Yield: 6.1 g of crystals (41%).

EXAMPLE 1

A. Methyl O-methyl podocarpate

The compound is prepared from podocarpic acid according to the method of Shaw, JOC, vol. 39, p. 1968, (1974), herein incorporated by reference.

$^1$H NMR (300 MHz, CDCl$_3$): δ6.98 (d, J=8 Hz, 1H); 6.83 (d, J=4 Hz, 1H); 6.70 (dd, J=4,8 Hz, 1H); 3.78 (s, 3H); 3.67 (s, 3H); 2.80 (m, 2H); 2.25 (m, 3H); 2.0 (m, 2H); 1.6 (m, 2H); 1.42 (m, 1H); 1.30 (s, 3H); 1.12 (m, 1H) and 1.05 (s, 3H).

MS: m/e 288 (M+).

B.

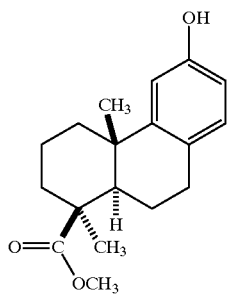

To a solution of 2.0 g (6.62 mmol) of the compound of Example 1A in 10 ml of 1,1,2 trichloroethane, was added 1.0 ml (7.0 mmol) of iodotrimethylsilane. The reaction mixture was heated to 70° C., reacted for 10 minutes, cooled, diluted with 150 ml of a 3:1 hexane/diethyl ether (hexane/Et$_2$O) mixture and then washed with a saturated sodium bicarbonate solution (NaHCO$_3$), dried over Na$_2$SO$_4$, filtered and concentrated in vacuo.

Yield: 1.51 g of a light tan solid (83%).

$^1$H NMR (300 MHz, CDCl$_3$): δ6.9 (d, J=8 Hz, 1H); 6.72 (d, J=4 Hz, 1H); 6.58 (dd, J=4,8 Hz, 1H); 4.55 (s, 1H); 3.63 (s, 3H); 2.75 (m, 2H); 2.20 (m, 3H); 1.95 (m, 2H); 1.57 (m, 2H); 1.4 (m, 1H); 1.25 (s, 3H); 1.08 (m, 1H) and 1.01 (s, 3H).

MS: m/e 274 (M+).

C.

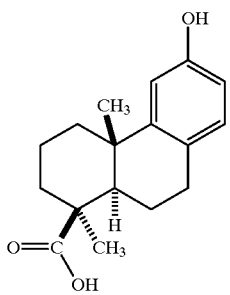

The compound was prepared substantially in accordance with the procedure detailed in Example 1B, using 1.0 g (3.31 mmol) of the compound of Example 1A, 1.0 ml (7.0=mol) of iodotrimethylsilane and 5 ml of 1,1,2-trichloroethane, with the exception that the saturated NaHCO$_3$ wash was acidified to pH 2. The desired compound was then extracted with CH$_2$Cl$_2$, and the extracts were dried over Na$_2$SO$_4$, filtered and then concentrated in vacuo to provide 100 mg of a white solid (11%).

$^1$H NMR (300 MHz, CDCl$_3$): δ6.93 (d, J=8 Hz, 1H); 6.73 (d, J=4 Hz, 1H); 6.6 (dd, J=4,8 Hz, 1H); 2.78 (m, 2H); 2.22 (m, 3H); 2.03 (m, 2H); 1.58 (m, 2H); 1.40 (m, 1H); 1.35 (s, 3H); 1.15 (s, 3H) and 1.10 (m, 1H).

Note: 780 mg of the compound of Example 1B was recovered.

EXAMPLE 2

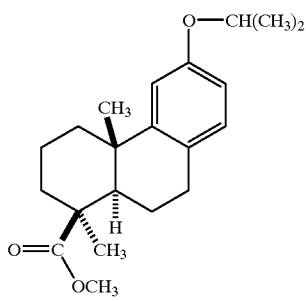

To a solution of 100 mg (0.35 mmol) of the compound of Example 1B in 2 ml of dimethylformamide (DMF), was added 62 mg (0.45 mmol) of K$_2$CO$_3$, followed by 42 μl (0.45 mmol) of isopropyl bromide. The reaction mixture was stirred for 2 hours at room temperature and then combined with an additional 180 mg (1.3 mmol) of K$_2$CO$_3$ and 130 μl (1.28 mmol) of isopropyl bromide. This mixture was stirred for 24 hours and then diluted with a 1:1 hexane/Et$_2$O mixture. The resultant layers were separated and the organic layer was washed sequentially with H$_2$O and 0.1N HCl, dried over Na$_2$SO$_4$, filtered and then concentrated in vacuo to provide an oily residue. This residue was purified using flash chromatography (SiO$_2$, eluent of 5% EtOAc in hexane).

Yield: 51 mg.

$^1$H NMR (300 MHz, CDCl$_3$): δ6.95 (d, J=8 Hz, 1H); 6.8 (d, J=4 Hz, 1H); 6.65 (dd, J=4,8 Hz, 1H); 4.47 (m, 1H); 3.64 (s, 3H); 2.78 (m, 2H); 2.22 (m, 3H); 1.97 (m, 2H); 1.58 (m, 2H); 1.40 (m, 1H); 1.32 (d, J=6 Hz, 3H); 1.28 (d, J=6 Hz, 3H); 1.10 (m, 1H) and 1.07 (s, 3H).

The compounds described in Examples 3–5 were prepared substantially in accordance with the procedure detailed in Example 2, using the shown starting materials.

EXAMPLE 3

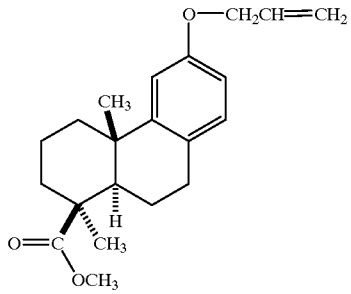

100 mg 0.35 mmol) of the compound of Example 1B, 242 mg (1.75 mmol) of K$_2$CO$_3$ and 169 μl (1.40 mmol) of allylbromide in 2 ml of DMF.

Yield.: 75 mg (65%)

$^1$H NMR (300 MHz, CDCl$_3$) δ6.97 (d, J=8 Hz, 1H); 6.83 (d, J=4 Hz, 1H); 6.68 (dd, J=4, 8 Hz, 1H); 6.07 (m, 1H); 5.35 (m, 2H); 4.50 (m, 2H); 3.68 (s, 3H); 2.78 (m, 2H); 2.23 (m, 3H); 1.98 (m, 2H); 1.58 (m, 2H); 1.40 (m, 1H); 1.28 (s, 3H); 1.10 (m, 1H) and 1.03 (s, 3H).

EXAMPLE 4

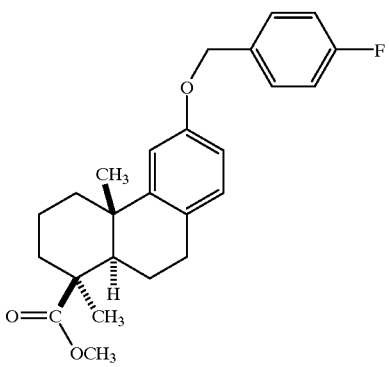

100 mg (0.35 mmol) of the compound of Example 1B, 93 mg (0.67 mmol) of K₂CO₃ and 81 μl (0.68 mmol) of 4-fluorobenzyl chloride in 2 ml of DMF.

Yield: 87 mg (63%).

$^1$H NMR (300 MHz, CDCl₃): δ7.4 (m, 2H); 7.08 (m, 2H); 6.98 (d, J=8 Hz, 1H); 6.88 (d, J=4 Hz, 1H); 6.74 (dd, J=4,8 Hz, 1H); 4.98 (s, 2H); 3.68 (s, 3H); 2.78 (m, 2H); 2.23 (m, 3H); 1.96 (m, 2H); 1.58 (m, 2H); 1.40 (m, 1H); 1.28 (s, 3H); 1.10 (m, 1H) and 1.03 (s, 3H).

EXAMPLE 5

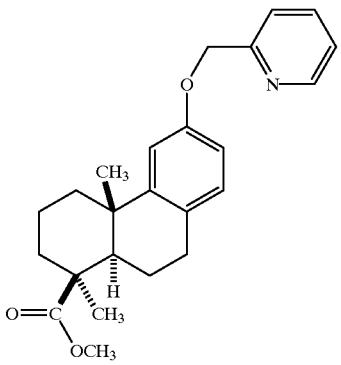

100 mg (0.35 mmol) of the compound of Example 1B, 180 mg (1.30 mmol) of K₂CO₃ and 107 mg (0.65 mmol) of 2-picolyl chloride hydrochloride in 2 ml of DMF.

Yield: 35 mg (26%).

$^1$H NMR (300 MHz, CDCl₃): δ8.58 (d, J=6 Hz, 1H); 7.70 (m, 1H); 7.52 (d, J=6 Hz, 1H); 7.20 (m, 1H); 6.95 (d, J=8 Hz, 1H); 6.89 (d, J=4 Hz, 1H); 6.74 (dd, J=4,8 Hz, 1H); 5.18 (s, 2H); 3.64 (s, 3H); 2.77 (m, 2H); 2.20 (m, 3H); 1.97 (m, 2H); 1.55 (m, 2H); 1.27 (s, 3H); 1.08 (m, 1H) and 1.0 (s, 3H)

EXAMPLE 6

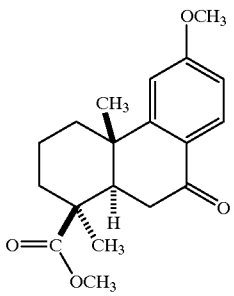

A solution of 6.58 g (65.04 mmol) of chromium trioxide in 70 ml of a 4:1 acetic acid (AcOH)/H₂O mixture was added to a mixture of 7.0 g (23.15 mmol) of the compound in Example 1A in 70 ml of AcOH. The reaction mixture was stirred for 18 hours resulting in the precipitation of a solid. This solid was isolated by filtration, washed with H₂O, dried in vacuo, redissolved in 75 ml of hot isopropanol (iPrOH) and filtered hot. The filtrate was combined with 225 ml of H₂O and cooled to 5° C. for 16 hours to provide crystals which were isolated by filtration, washed with H₂O and dried in vacuo at 45° C.

Yield: 6.31 g (86%).

$^1$H NMR (300 MHz, CDCl₃): δ8.04 (d, J=8 Hz, 1H); 6.88 (d, J=4 Hz, 1H); 6.82 (dd, J=8,4 Hz, 1H); 3.87 (s, 3H); 3.72 (s, 3H); 3.18 (m, 1H); 2.95 (m, 1H); 2.33 (m, 2H); 2.05 (m, 2H); 1.72 (m, 1H); 1.55 (m, 1H); 1.25 (s, 3H); 1.16 (m, 1H) and 1.11 (s, 3H).

MS: m/e 316 (M+).

Elemental Analysis for C₁₉H₂₄O₄: Calcd: C, 72.13; H, 7.65; Found: C, 72.15; H, 7.79.

EXAMPLE 7

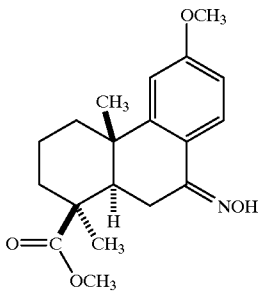

To a solution of 316 mg (1.0 mmol) of the compound of Example 6 in 3.0 ml of absolute ethanol (EtOH), was added 80 mg (1.15 mmol) of hydroxylamine hydrochloride followed by 94 mg (1.15 mmol) of sodium acetate (NaOAc). The reaction mixture was stirred for 65 hours at room temperature and then concentrated in vacuo to provide a solid which was partitioned between Et₂O and H₂O. The resultant layers were separated and the organic layer was dried over Na₂SO₄, filtered and concentrated in vacuo to provide a solid. This solid was redissolved in 0.5 ml of Et₂O and 8 ml of hot hexane and then cooled to 0° C. resulting in the formation of crystals.

Yield: 282 mg (85%).

$^1$H NMR (300 MHz, CDCl₃): δ8.0 (s, 1H); 7.88 (d, J=8 Hz, 1H); 6.88 (d, J=4 Hz, 1H); 6.78 (dd, J=4,8 Hz, 1H); 3.82

(s, 3H); 3.74 (s, 3H); 3.45 (m, 1H); 3.07 (m, 1H); 2.30 (m, 2H); 2.02 (m, 1H); 1.72 (m, 2H); 1.57 (m, 1H); 1.35 (s, 3H); 1.13 (m, 1H) and 1.0 (s, 3H).

MS: m/e 331 (M+).

Elemental Analysis for $C_{19}H_{25}NO_4$: Calcd: C, 68.86; H, 7.60; N, 4.23; Found: C, 69.12; H, 7.69; N, 4.21.

EXAMPLE 8

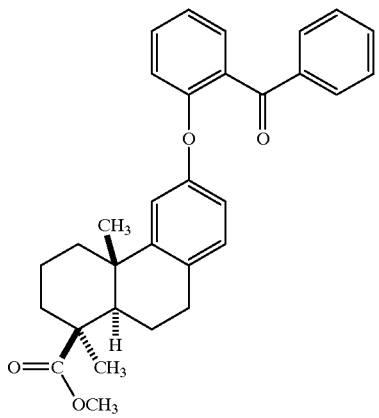

To a hot (100° C.) solution of 426 mg (1.48 mmol) of the compound in Example 1B in 3.0 ml of collidine, was added 0.45 ml (2.66 mmol) of 2-fluorobenzophenone, 415 mg (3.0 mmol) of $K_2CO_3$ and 444 mg (5.58 mmol) of copper (II) oxide (CuO). The reaction mixture was then heated to 171° C. and reacted for 16 hours. After cooling, the mixture was diluted with 50 ml of $Et_2O$, washed with 20 ml of 1N HCl, dried over $Na_2SO_4$, filtered and then concentrated in vacuo to provide a brown oil. This oil was purified using radial chromatography (4000 micron plate, gradient eluent of 75–100% $CH_2Cl_2$ in hexane).

Yield: 352 mg (51%).

$^1$H NMR (300 MHz, $CDCl_3$): δ7.82 (d, J=6 Hz, 2H); 7.45 (m, 5H); 7.18 (m, 1H); 6.90 (m, 2H); 6.75 (m, 1H); 6.58 (m, 1H); 3.67 (s, 3H); 2.77 (m, 2H); 2.20 (m, 2H); 1.95 (m, 3H); 1.60 (m, 1H); 1.47 (m, 1H); 1.35 (m, 1H); 1.27 (s, 3H); 1.02 (n, 1H) and 0.95 (s, 3H).

MS: m/e 469 (M+).

Elemental Analysis for $C_{31}H_{32}O_4$: Calcd: C, 79.46; H, 6.88; Found: C, 79.53; H, 7.06.

EXAMPLE 9

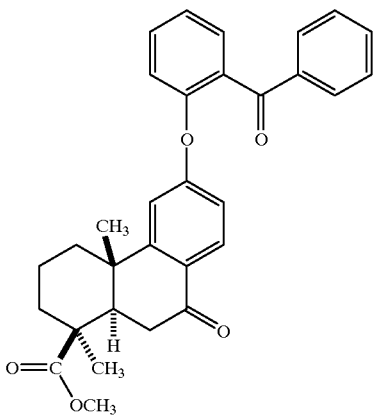

The compound was prepared substantially in accordance with the procedure detailed in Example 6, using 260 mg (0.56 mmol) of the compound of Example 8, 158 mg (1.56 mmol) of chromium trioxide in 3.05 ml AcOH/0.34 ml $H_2O$.

Yield: 231 mg (86%).

$^1$H NMR (300 MHz, $CDCl_3$): δ7.90 (d, J=8 Hz, 1H); 7.75 (m, 2H); 7.55 (m, 3H); 7.35 (m, 3H); 7.10 (d, J=8 Hz, 1H); 6.72 (d, J=4 Hz, 1H); 6.62 (dd, J=4,8 Hz, 1H); 3.70 (s, 3H); 3.15 (m, 1H); 2.93 (m, 1H); 2.30 (m, 1H); 2.0 (m, 3H); 1.63 (m, 1H); 1.38 (m, 1H); 1.23 (s, 3H); 1.10 (m, 1H) and 1.0 (s, 3H)

MS: m/e 483 (M+).

Elemental Analysis for $C_{31}H_{30}O_5$: Calcd: C, 77.16; H, 6.27; Found: C, 76.96; H, 6.29.

EXAMPLE 10

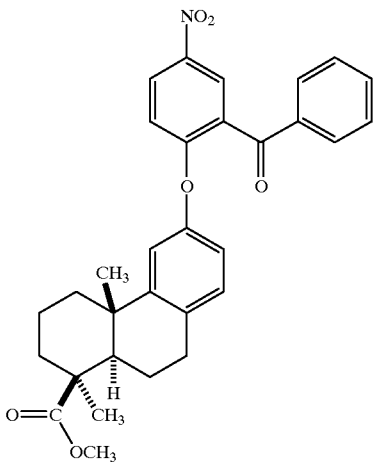

The compound was obtained from the Bader chemical collection, Aldrich Chemical Company.

$^1$H NMR (300 MHz, $CDCl_3$): δ8.38 (d, J=4 Hz, 1H); 8.23 (dd, J=4,8 Hz, 1H); 7.87 (d, J=6 Hz, 2H); 7.60 (m, 1H); 7.48 (t, J=6 Hz, 2H); 7.03 (d, J=8 Hz, 1H); 6.85 (m, 2H); 6.68 (dd, J=4, 8Hz, 1H); 3.64 (s, 3H); 2.80 (m, 2H); 2.22 (m, 2H); 1.98 (m, 3H); 1.55 (m, 2H); 1.33 (m, 1H); 1.26 (S, 3H); 1.07 (m, 1H) and 0.97 (S, 3H).

MS: m/e 513 (M+).:

Elemental Analysis for $C_{31}H_{31}NO_6$: Calcd: C, 72.50; H. 6.08; N. 2.73 Found: C, 72.40; H, 6.11; N. 2.66.

EXAMPLE 11

A.

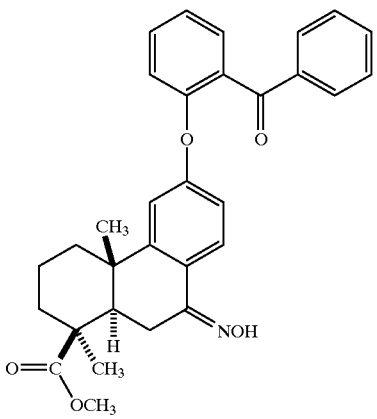

The compound was prepared substantially in accordance with the procedure detailed in Example 7, using 150 mg (0.311 mmol) of the compound of Example 9, 22 mg (0.311 mmol) of hydroxylamine hydrochloride and 26 mg (0.311 mmol) of NaOAc in 3.0 ml of EtOH. The crude material was purified using radial chromatography (2000 micron plate, eluent of 5% EtOAc in $CH_2Cl_2$).

Yield: 138 mg (89%).

$^1$H NMR (300 MHz, $CDCl_3$): δ7.78 (m, 3H); 7.45 (m, 5H); 7.25 (m, 1H); 7.0 (d, J=8 Hz, 1H); 6.75 (d, J=4HZ, 1H); 6.62 (dd, J=4,8 Hz, 1H); 3.70 (S, 3H); 3.4 (m, 1H); 3.02 (m, 1H); 2.25 (m, 1H); 1.98 (m, 2H); 1.63 (m, 2H); 1.37 (m, 1H); 1.30 (S, 3H); 1.08 (m, 1H) and 0.92 (s, 3H).

MS: m/e 497 (M+).

B.

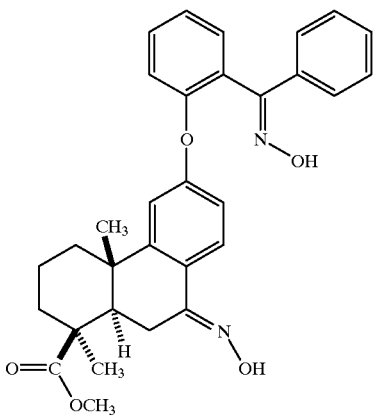

The compound was isolated from the reaction mixture of Example 11A.

Yield: 5 mg.

$^1$H NMR (300 MHz, $CDCl_3$): δ7.65 (d, J=8 Hz, 1H); 7.50 (m, 2H) 7.30 (m, 6H); 7.02 (d, J=8 Hz, 1H); 6.90 (d, J=4 Hz, 1H); 6.78 (dd, J=4,8 Hz, 1H); 3.69 (s, 3H); 3.4 (m, 1H); 3.02 (m, 1H); 2.2 (m, 2H); 1.95 (m, 1H); 1.63 (m, 2H); 1.42 (m, 1H); 1.30 (s, 3H); 1.08 (m, 1H) and 0.95 (s, 3H).

MS: m/e 512 (M+).

C.

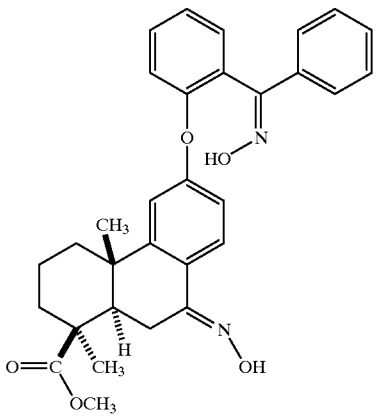

The compound was isolated from the reaction mixture of Example 11A.

Yield: 4 mg $^1$H NMR (300 MHz, $CDCl_3$): δ7.68 (t, J=8 Hz, 1H); 7.50 (m, 1H); 7.30 ((m, 5H); 6.85 (m, 3H); 6.58 (d, J=4 Hz, 1H); 6.44 (dd, J=4,8 Hz, 1H); 3.68 (s, 3H); 3.38 (m, 1H); 3.0 (m, 1H); 2.24 (m, 1H); 2.0 (m, 2H); 1.63 (m, 2H); 1.37 (m, 1H); 1.30 (s, 3H); 1.07 (m, 1H) and 0.92 (s, 3H).

MS: m/e 512 (M+).

EXAMPLE 12

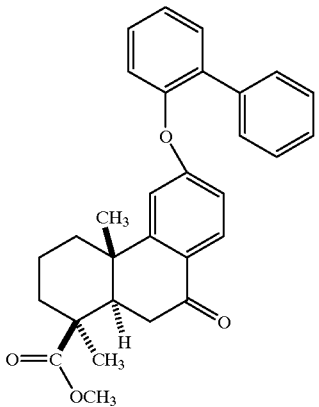

The compound was prepared substantially in accordance with the procedure detailed in Example 8, using 100 mg (0.347 mmol) of the compound of Example 1B, 98 mg (0.423 mmol) of 2-bromobiphenyl, 97 mg (0.702 mmol) of $K_2CO_3$ and 70 mg (0.88 mmol) of CuO in 1.5 ml of collidine. The crude material was purified using column chromatography (eluent of 30% hexane in $CH_2Cl_2$)

Yield: 81 mg (53%)

$^1$H NMR (300 MHz, $CDCl_3$): δ7.58 (m, 2H); 7.25 (m, 6H); 6.95 (m, 2H); 7.88 (d, J=4 Hz, 1H); 6.70 (dd, J=4,8 Hz, 1H); 3.64 (s, 3H); 2.78 (m, 2H); 2.15 (m, 3H); 1.95 (m, 2H); 1.55 (m, 2H); 1.35 (m, 1H); 1.25 (s, 3H); 1.05 (m, 11H) and 0.97 (s, 3H).

MS: m/e 440 (M+).

EXAMPLE 13

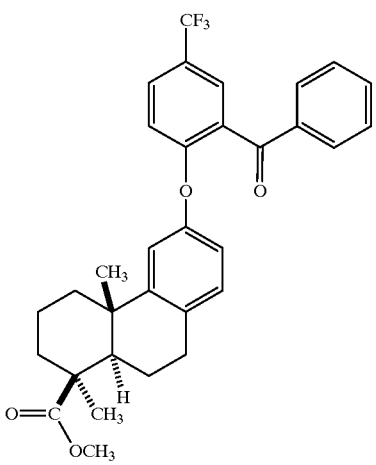

The compound was prepared substantially in accordance with the procedure detailed in Example 8, using 500 mg (1.74 mmol) of the compound of Example 1B, 950 mg (3.54 mmol) of 2-fluoro-5-(trifluoromethyl)benzophenone, 500 mg (3.62 mmol) of $K_2CO_3$, and 350 mg (4.35 mmol) of CuO in 8.0 ml collidine. The crude material was purified using radial chromatography (4000 micron plate, eluent of 25% hexane in $CH_2Cl_2$).

Yield: 670 mg (72%).

$^1$H NMR (300 MHz, $CDCl_3$): δ7.84 (d, J=8 Hz, 2H); 7.75 (m, 1H); 7.57 (m, 2H); 7.45 (t, J=8 Hz, 2H); 6.97 (d, J=8 Hz, 1H); 6.89 (d, J=8 Hz, 1H); 6.80 (d, J=4 Hz, 1H); 6.62 (dd, J=4,8 Hz, 1H); 3.62 (s, 3H); 2.78 (m, 2H); 2.20 (m, 2H); 1.98 (m, 3H); 1.55 (m, 2H); 1.30 (m, 1H); 1.25 (s, 3H); 1.08 (m, 1H) and 0.96 (s, 3H).

MS: m/e 536 (M+).

EXAMPLE 14

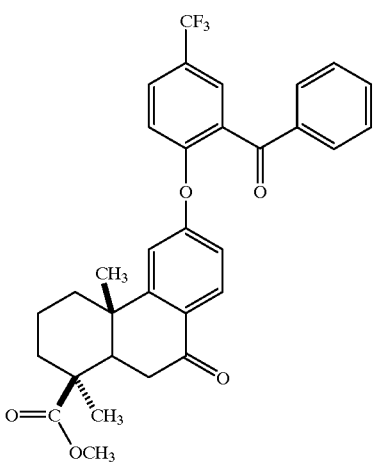

The compound was prepared substantially in accordance with the procedure detailed in Example 6, using 75 mg (0.14 mmol) of the compound of Example 13, 40 mg (0.40 mmol) of chromium trioxide in a 0.85 ml AcOH/0.1 ml $H_2O$ mixture.

Yield: 49 mg (64%).

$^1$H NMR (300 MHz, $CDCl_3$): δ7.95 (d, J=6 Hz, 1H); 7.77 (m, 3H); 7.58 (m, 1H); 7.42 (t, J=6 Hz, 2H); 7.12 (d, J=8 Hz, 1H); 6.80 (d, J=4 Hz, H); 6.70 (dd, J=4,8 Hz, 1H); 3.68 (s, 3H); 3.18 (m, 1H); 2.95 (m, 1H); 2.30 (m, 1H); 2.0 (m, 3H); 1.67 (m, 1H) 1.40 (m, 1H); 1.25 (s, 3H); 1.12 (m, 1H) and 1.03 (s, 3H).

MS: m/e 550 (M+).

EXAMPLE 15

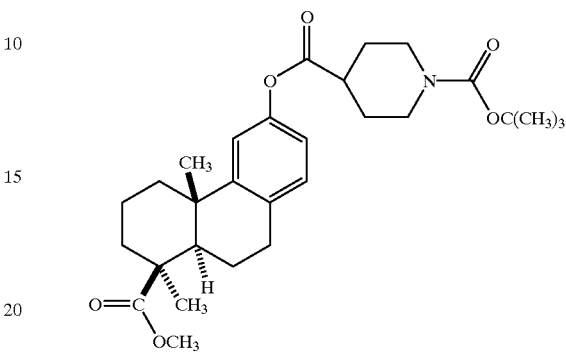

To a solution of 200 mg (0.694 mmol) of the compound of Example 1B in 5.0 ml of $CH_2Cl_2$, was added 0.372 ml (2.10 mmol) of diisopropylethylamine and 86 mg (0.70 mmol) of 4-dimethylamino pyridine followed by a mixture containing 480 mg (2.10 mmol) of the compound of Preparation 1, 0.207 ml (2.56 mmol) of pyridine and 0.170 ml (2.33 mmol) of thionyl chloride in 5.0 ml of $CH_2Cl_2$. The reaction mixture was stirred at room temperature for 30 minutes, diluted with $CH_2Cl_2$, washed sequentially with 1N HCl and a saturated $NaHCO_3$ solution, dried over $Na_2SO_4$, filtered and then concentrated in vacuo to provide a tan foam. This foam was purified using radial chromatography (2000 micron plate, gradient eluent of 10% hexane in $CH_2Cl_2$ to 25% EtOAc in $CH_2Cl_2$).

Yield: 280 mg (81%).

$^1$H NMR (300 MHz, $CDCl_3$): δ7.02 (d, J=8 Hz, 1H); 6.90 (d, J=4 Hz, 1H); 6.77 (dd, J=4,8 Hz, 1H): 4.08 (m, 2H); 3.65 (s, 3H); 2.90 (m, 3H); 2.75 (m, 3H); 2.20 (m, 3H); 1.98 (m, 4H); 1.78 (m, 2H); 1.6 (m, 1H); 1.45 (s, 9H); 1.40 (m, 1H); 1.28 (s, 3H); 1.08 (m, 1H) and 1.0 (s, 3H).

MS: m/e 499 (M+).

EXAMPLE 16

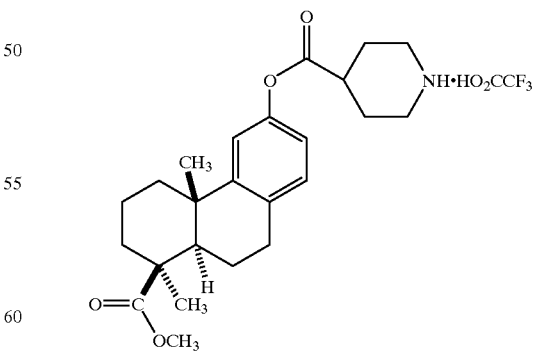

To a solution of 250 mg (0.50 mmol) of the compound in Example 15 in 1.0 ml of $CH_2Cl_2$, was added 0.160 ml (1.0 mmol) of triethylsilane and 1.0 ml of trifluoroacetic acid ($CF_3COOH$). The reaction mixture was stirred for 30 minutes at room temperature, diluted with 15 ml of acetonitrile (CH₃CN) and then concentrated in vacuo to provide 231 mg of a tan solid. Then, 200 mg of this solid was dissolved in 20 ml of CH₂Cl₂, washed with a saturated NaHCO₃ solution, dried over Na₂SO₄, filtered and concentrated in vacuo.

Yield: 170 mg (98%).

¹H NMR (300 MHz, CDCl₃): δ7.02 (d, J=8 Hz, 1H); 6.92 (d, J=4 Hz, 1H); 6.78 (dd, J=4,8 Hz, 1H); 3.63 (s, 3H); 3.17 (m, 2H); 2.75 (m, 5H); 2.20 (m, 3H); 1.98 (m, 4H); 1.75 (m, 2H); 1.58 (m, 2H); 1.40 (m, 1H); 1.27 (s, 3H); 1.08 (m, 1H) and 1.0 (s, 3H).

MS: m/e 400 (M+).

EXAMPLE 17

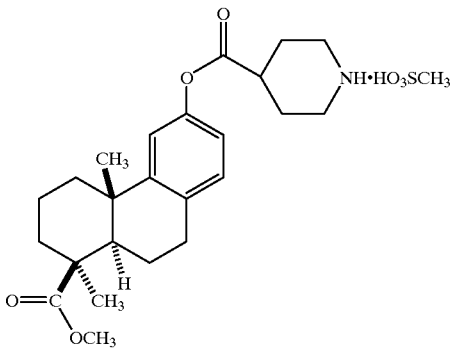

To a solution of 160 mg (0.4 mmol) of the free base of the compound of Example 16 in 4.0 ml of a 3:1 Et₂O/hexane mixture, was added 26 μl (0.4 mmol) of methanesulfonic acid.

Yield: 198 mg of a solid (quantitative).

¹H NMR (300 MHz, CDCl₃): δ8.43 (bs, 1H); 8.20 (bs, 1H); 6.75 (d, J=8 Hz, 1H); 6.60 (d, J=4 Hz, 1H); 6.45 (dd, J=4,8 Hz, 1H); 3.55 (s, 3H); 3.20 (m, 2H); 2.90 (m, 2H); 2.58 (m, 3H); 2.30 (s, 3H); 2.10 (m, 3H); 1.93 (m, 4H); 1.65 (m, 2H); 1.47 (m, 2H); 1.24 (m, 1H); 1.17 (s, 3H); 1.08 (m, 1H) and 0.88 (s, 3H).

EXAMPLE 18

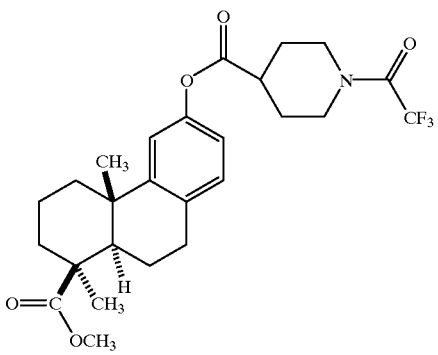

To a solution of 160 mg (0.324 mmol) of the compound in Example 17 in 3.0 ml CH₂CO₂, was added 100 μl (0.712 mmol) of Et₃N and 50 μl (0.356 mmol) of trifluoroacetic anhydride. The reaction mixture was stirred for 15 minutes at room temperature, diluted with 30 ml of EtOAc, sequentially washed with 10 ml of 0.2N HCl, 10 ml of a saturated NaHCO₃ solution and 10 ml brine, dried over NaSO₄, filtered and then concentrated in vacuo.

Yield: 130 mg (81%).

¹H NMR (300 MHz, CDCl₃): δ7.03 (d, J=8 Hz, 1H); 6.91 (d, J=4 Hz, 1H); 6.78 (dd, J=4,8 Hz, 1H); 4.37 (m, 1H); 4.0 (m, 1H); 3.64 (s, 3H); 3.35 (m, 1H); 3.15 (m, 1H); 2.82 (m, 3H) 2.28 (m, 1H); 2.18 (m, 4H); 1.95 (m, 3H); 1.50 (m, 4H); 1.25 (s, 3H); 1.08 (m, 1H) and 1.0 (s, 3H).

EXAMPLE 19

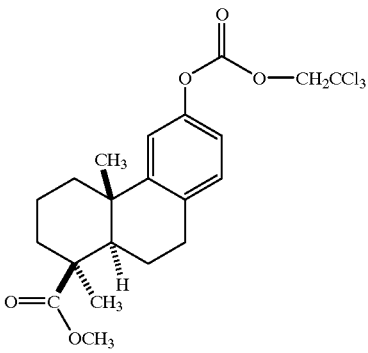

To a solution of 470 mg (1.63 mmol) of the compound of Example 1B in 12.0 ml of a 1:2 Et₂O/CH₂Cl₂ mixture, was added 0.237 ml (1.70 mmol) of Et₃N and 0.224 ml (1.63 mmol) of 2,2,2-trichloroethyl chloroformate. The reaction mixture was stirred at room temperature for 20 minutes, diluted with 50 ml of Et₂O, sequentially washed with 15 ml of H₂O, 15 ml of 0.2N HCl, 15 ml of NaCO₃ and 15 ml of brine, dried over Na₂SO₄, filtered and then concentrated in vacuo to provide an oily residue. This residue was purified using flash chromatography (SiO₂, eluent of 30% hexane in CH₂Cl₂).

Yield: 620 mg (82%).

¹H NMR (300 MHz, CDCl₃): δ7.08 (m, 2H); 6.93 (m, 1H); 4.87 (s, 2H); 3.67 (s, 3H); 2.90 (m, 1H); 2.78 (m, 1H); 2.23 (m, 3H); 2.00 (m, 2H); 1.58 (m, 2H); 1.42 (m, 1H); 1.30 (s, 3H); 1.12 (m/, H) and 1.03 (s, 3H).

MS: m/e 463 (M+).

EXAMPLE 20

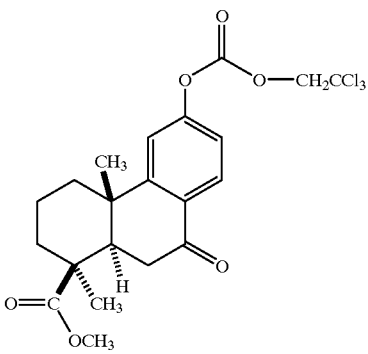

The compound was prepared substantially in accordance with the procedure detailed in Example 6, using 620 mg (1.33 mmol) of the compound of Example 19, 405 mg (4.0 mmol) of chromium trioxide in a 8.1 ml AcOH/0.9 ml H₂O.

Yield: 540 mg (85%).

¹H NMR (300 MHz, CDCl₃): δ8.02 (d, J=8 Hz, 1H); 6.90 (d, J=4 Hz, 1H); 6.80 (dd, J=4,8 Hz, 1H); 5.02 (s, 2H); 3.70 (s, 3H); 3.18 (m, 1H); 2.83 (m, 1H); 2.30 (m, 2H); 2.03 (m, 2H); 1.70 (m, 1H); 1.50 (m, 1H); 1.25 (s, 3H); 1.10 (m, 1H) and 1.02 (s, 3H).

EXAMPLE 21

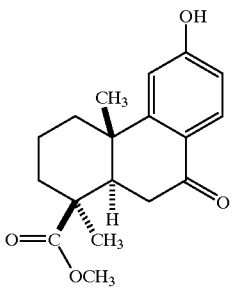

To a solution of 5.3 g (11.1 mmol) of the compound of Example 20 in 90 ml of a 1:2 AcOH/EtOH mixture, was added 10.0 g (153 mmol) of zinc dust. The mixture was reacted for 5 minutes at 80° C. and then cooled to room temperature, filtered and concentrated in vacuo to provide a solid. This solid was slurried in CH₂Cl₂ and filtered. The filtrate was dried in vacuo to provide a solid which was diluted with 100 ml of hot CHCl₃ and filtered into 700 ml of hexane. The compound was then crystallized from this solution.

Yield: 3.31 g (99%).

¹H NMR (300 MHz, CDCl₃): δ7.82 (d, J=8 Hz, 1H): 6.80 (d, J=4 Hz, 1H); 6.70 (dd, J=4,8 Hz, 1H); 3.68 (s, 3H); 3.15 (m, 1H); 2.82 (m, 1H); 2.26 (m, 2H); 2.03 (m, 2H); 1.67 (m, 1H); 1.50 (m, 1H); 1.20 (s, 3H); 1.17 (m, 1H) and 1.08 (s, 3H).

MS: m/e 302 (M+).

EXAMPLE 22

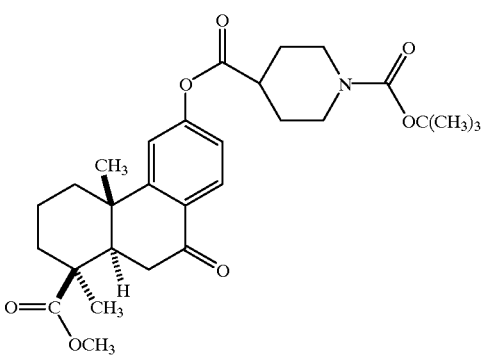

The compound was prepared substantially in accordance with the procedure detailed in Example 15, using 440 mg (1.46 mmol) of the compound of Example 21, 0.645 ml (3.7 mmol) of diisopropylethylamine, 179 mg (1.46 mmol) of 4-dimethylaminopyridine, 845 mg (3.7 mmol) of the compound of Preparation 1, 0.365 ml (4.5 mmol) of pyridine and 0.300 (4.1 mmol) of thionyl chloride in 45 ml of CH₂Cl₂.

Yield: 380 mg (51%).

¹H NMR (300 MHz, CDCl₃): δ8.08 (d, J=8 Hz, 1H); 7.10 (d, J=4 Hz, 1H); 7.0 (dd, J=4,8 Hz, 1H); 4.08 (m, 2H); 3.71 (s, 3H); 3.22 (m, 1H); 2.95 (m, 3H); 2.72 (m, 1H); 2.30 (m, 2H); 2.05 (m, 4H); 1.75 (m, 3H) 1.47 (s, 9H); 1.26 (s, 3H); 1.16 (m, 1H) and 1.14 (s, 3H).

MS: m/e 513 (M+).

EXAMPLE 23

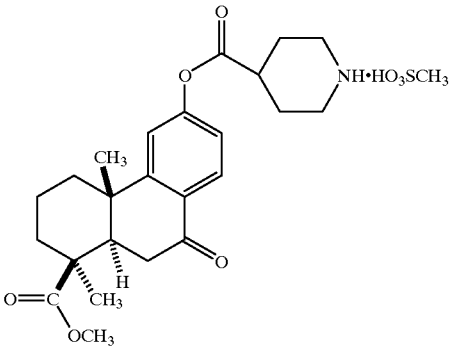

The compound was prepared substantially in accordance with the procedures detailed in Examples 16 and 17, using 160 mg (0.31 mmol) of the compound of Example 22, 0.1 ml (0.63 mmol) of triethylsilane, 2.0 ml of a 1:1 CF₃COOH/CH₂Cl₂ mixture and 20 μl (0.31 mmol) of methanesulfonic acid.

Yield: 153 mg (97%).

¹H NMR (300 MHz, CDCl₃): δ8.05 (m, 1H); 7.10 (m, 1H); 7.0 (m, 1H); 3.65 (s, 3H); 3.18 (m, 3H); 2.95 (m, 2H); 2.65 (m, 3H); 2.27 (bs, 3H); 2.05 (m, 5H); 1.75 (m, 3H); 1.50 (m, 1H); 1.23 (s, 3H); 1.18 (m, 1H) and 1.10 (s, 3H).

EXAMPLE 24

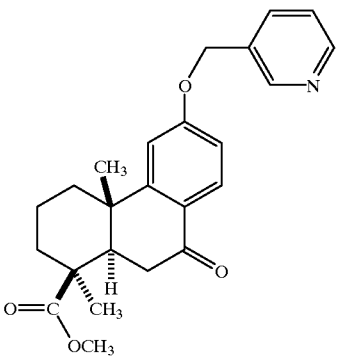

To a solution of 250 mg (0.83 mmol) of the compound from Example 21 in 8.0 ml of tetrahydrofuran (THF), was added 85 μl (0.87 mmol) of 3-pyridylcarbinol, 236 mg (0.9 mmol) of triphenylphosphine and 142 μl (0.9 mmol) of diethyl azodicarboxylate. The reaction mixture was heated to 65° C. and reacted for 10 minutes, cooled to room temperature and concentrated in vacuo to provide an oily residue. This residue was triturated in Et₂O and filtered. The filtrate was washed sequentially with H₂O and a 0.1N K₂CO₃ solution, dried over Na₂SO₄, filtered and concentrated in vacuo.

Yield: 198 mg of a tan solid (61%).

¹H NMR (300 MHz, CDCl₃): δ8.70 (s, 1H); 8.60 (d, J=4 Hz, 1H); 8.05 (d, J=8 Hz, 1H); 7.78 (d, J=8 Hz, 1H); 7.35

(m, 1H); 6.95 (d, J=4 Hz, 1H); 6.90 (dd, J=4,8 Hz, 1H); 5.13 (s, 2H); 3.70 (s, 3H); 3.18 (m, 1H); 2.95 (m, 1H); 2.30 (m, 2H); 2.04 (m, 2H); 1.70 (m, 1H); 1.53 (m, 1H); 1.25 (s, 3H); 1.13 (m, 1H) and 1.10 (s, 3H).

MS: m/e 393 (M+).

EXAMPLE 25

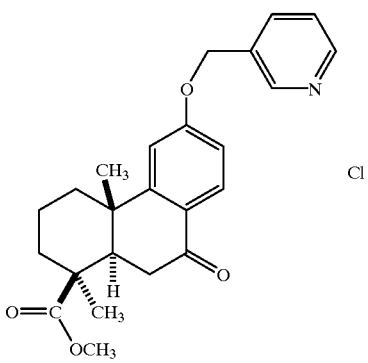

To a solution of 38 mg (0.097 mmol) of the compound from Example 24 in 2.2 ml of a 1:1:0.2 $CH_3CN/Et_2O$/hexane mixture, was added 0.1 ml of a $HCl/CH_3CN$ solution (1.0 ml of concentrated HCl in 11.0 ml of $CH_3CN$) which resulted in the formation of a precipitate. This precipitate was isolated by filtration.

Yield: 40 mg (96%).

$^1$H NMR (300 MHz, $CDCl_3$): δ5.80 (bs, 1H); 8.65 (s, 1H); 8.55 (d, J=4 Hz, 1H); 7.98 (d, J=8 Hz, 1H); 7.72 (d, J=8 Hz, 1H); 7.30 (m, 1H); 6.90 (d, J=4 Hz, 1H); 6.83 (dd, J=4,8 Hz, 1H); 5.10 (s, 2H); 3.68 (s, 3H); 3.16 (m, 1H); 2.91 (m, 1H); 2.27 (m, 2H); 2.0 (m, 2H); 1.68 (m, 1H); 1.50 (m, 1H); 1.23 (s, 3H); 1.10 (m, 1H) and 1.03 (s, 3H).

MS: m/e 393 (M+-HCl).

EXAMPLE 26

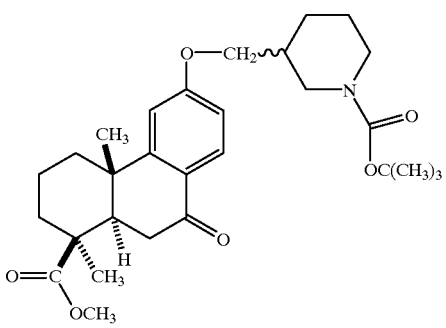

The compounds were prepared substantially in accordance with the procedure detailed in Example 24, using 300 mg (0.992 mmol) of the compound of Example 21, 214 mg (0.992 mmol) of the compound of Preparation 2, 275 mg (1.05 mmol) of triphenylphosphine and 0.165 ml (1.05 mmol) of diethylazodicarboxylate in 9.0 ml of THF. The crude material was purified using radial chromatography (2000 micron plate, eluent of 5% EtOAc in $CH_2Cl_2$).

Yield: 477 mg (96%).

$^1$H NMR (300 MHz, $CDCl_3$): δ8.01 (d, J=8 Hz, 1H); 6.84 (d, J=4 Hz, 1H); 6.78 (dd, J=4,8 Hz, 1H); 3.85 (m, 3H); 3.70 (s, 3H); 3.17 (m, 1H); 2.92 (m, 2H); 2.30 (m, 2H); 2.02 (m, 3H); 1.88 (m, 1H); 1.68 (m, 3H); 1.50 (m, 4H); 1.46 (s, 9H); 1.26 (s, 3H); 1.13 (m, 1H) and 1.10 (s, 3H).

MS: m/e 499 (M+).

EXAMPLE 27

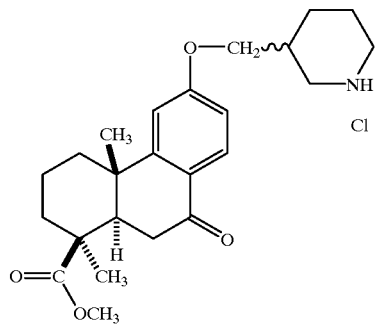

The compounds were prepared substantially in accordance with the procedures detailed in Examples 16 and 25, using 378 mg (0.76 mmol) of the compound of Example 26, 0.20 ml (1.26 mmol) of triethylsilane, 5.0 ml of a 2:3 $CH_2Cl_2/CF_3COOH$ mixture and 0.714 ml of a $HCl/CH_3CN$ solution (1.0 ml of concentrated HCl in 11.0 ml of $CH_3CN$).

Yield: 287 mg (87%).

$^1$H NMR (300 MHz, $CDCl_3$): δ9.02 (m, 2H); 7.80 (d, J=8 Hz, 1H); 6.95 (s, 1H); 6.87 (d, J=8 Hz, 1H); 3.97 (m, 2H); 3.60 (s, 3H); 3.22 (m, 1H); 3.03 (m, 1H); 3.74 (m, 3H); 2.20 (m, 5H); 1.75 (m, 5H); 1.35 (m, 2H); 1.18 (s, 3H); 1.13 (m, 1H) and 1.0 (s, 3H).

MS: m/e 399 (M+-HCl).

EXAMPLE 28

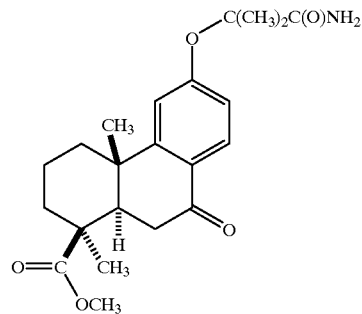

To a solution of 1.2 g (3.97 mmol) of a compound of Example 21 in 50 ml of dioxane, was slowly added 210 mg (4.37 mmol) of a 50% dispersion of sodium hydride (NaH) in mineral oil, with stirring, followed by 663 mg (3.97 mmol) of the compound from Preparation 3. The mixture was heated to 100° C. and reacted for 6 hours, then cooled and combined with 5.0 ml of 1N sodium hydroxide (NaOH), followed by 200 ml of EtOAc. The resultant layers were separated and the organic layer was dried over $Na_2SO_4$, filtered and concentrated in vacuo.

Yield: 500 mg (32%).

$^1$H NMR (300 MHz, $CDCl_3$): δ7.98 (d, J=8 Hz, 1H); 6.90 (d, J=4 Hz, 1H); 6.83 (dd, J=4,8 Hz, 1H); 6.40 (bs, 1H); 5.6 (bs, 1H); 3.70 (s, 3H); 3.18 (m, 1H); 2.95 (m, 1H); 2.28 (m, 2H); 2.02 (m, 2H); 1.70 (m, 1H); 1.61 (s, 3H); 1.58 (s, 3H); 1.48 (m, 1H); 1.25 (s, 3H); 1.13 (m, 1H) and 1.10 (s, 3H).

EXAMPLE 29

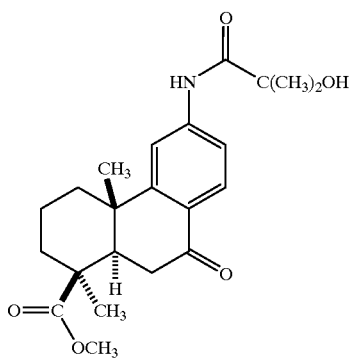

To a solution of 480 mg (1.23 m mol) of the compound of Example 28 in a mixture of 15.0 ml DMF and 2.0 ml of 1,3-dimethyl-3,4,5,6-tetrahydro-2(1H)-pyrimidinone, was added 66 mg (1.36 mmol) of a 50% dispersion of NaH in mineral oil. The reaction mixture was refluxed for 5 minutes and then cooled to room temperature. To the mixture, was added 10 ml of a saturated $NaHCO_3$ solution followed by 100 ml of EtOAc. The resultant layers were separated and the organic layer was sequentially washed with $H_2O$ and 0.2N HCl, dried over $Na_2SO_4$, filtered and concentrated in vacuo.

Yield: 380 mg of a tan solid (79%).

$^1$H NMR (300 MHz, $CDCl_3$): δ8.90 (bs, !H); 8.02 (d, J=8 Hz, 1H); 7.92 (d, J=4 Hz, 1H); 7.32 (dd, J=4,8 Hz, 1H); 3.70 (s, 3H); 3.22 (m, 1H); 2.97 (m, 1H); 2.35 (m, 3H); 2.05 (m, 2H); 1.70 (m, 1H); 1.57 (s, 6H); 1.52 (m, 1H); 1.25 (s, 3H); 1.15 (m, 1H) and 1.12 (s, 3H).

MS: m/e 387 (M+).

EXAMPLE 30

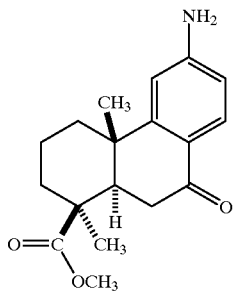

To a solution of 100 mg (0.257 mmol) of the compound of Example 29 in 5.0 ml of dioxane, was added 0.8 ml of 5N HCl. The reaction mixture was heated to 100° C., reacted for 2 hours, cooled and then diluted with 50 ml of $CH_2Cl_2$. The resultant layers were separated and the organic layer was washed with a saturated $NaHCO_3$ solution dried over $Na_2SO_4$, filtered and concentrated in vacuo to provide a solid. This solid was purified using radial chromatography (1000 micron plate, eluent of 20% EtOAc in $CH_2Cl_2$).

Yield: 46 mg (60%).

$^1$H NMR (300 MHz, $CDCl_3$): δ7.90 (d, J=8 Hz, 1H); 6.55 (m, 2H); 4.12 (bs, 2H); 3.70 (s, 3H); 3.15 (m, 1H); 2.90 (m, 1H); 2.27 (m, 2H); 2.02 (m, 2H); 1.67 (m, 1H); 1.50 (m, 1H); 1.22 (s, 3H); 1.12 (m, 1H) and 1.08 (s, 3H).

MS: m/e 301 (M+).

EXAMPLE 31

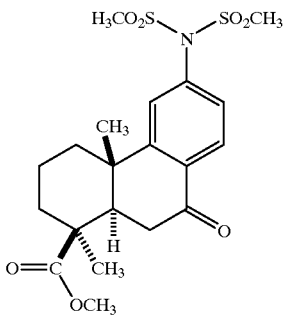

To a solution of 25 mg (0.083 mmol) of the compound of Example 30 in 1.0 ml $CH_2Cl_2$, was slowly added 24 μl (0.172 mmol) of $Et_3N$ and 13 μl (0.168 mmol) of methanesulfonyl chloride. The reaction mixture was diluted with EtOAc and washed sequentially with 0.2N HCl and a saturated $NaHCO_3$ solution, dried over $Na_2SO_4$, filtered and concentrated in vacuo.

Yield: 31 mg of a white solid (82%).

$^1$H NMR (300 MHz, $CDCl_3$): δ8.13 (d, J=8 Hz, 1H); 7.4 (s, 1H); 7.30 (d, J=8 Hz, 1H); 3.73 (s, 3H); 3.40 (s, 6H); 3.25 (m, 1H); 3.03 (m, 1H); 2.35 (m, 2H); 2.05 (m, 2H): 1.75 (m, 1H); 1.58 (m, 1H); 1.27 (s, 3H); 1.16 (m, 1H) and 1.15 (s, 3H).

EXAMPLE 32

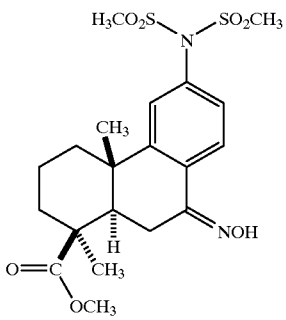

The compound was prepared substantially in accordance with the procedure detailed in Example 7, using 24 mg (0.053 mmol) of the compound of Example 31, 4.6 mg (0.066 mmol) of hydroxylamine hydrochloride and 5.4 mg (0.066 mmol) of NaoAc in 1.0 ml of EtOH. The crude material was purified using radial chromatography (1000 micron plate, eluent of 5% EtOAc in $CH_2Cl_2$).

Yield: 20 mg (80%).

$^1$H NMR (300 MHz, $CDCl_3$): δ8.0 (d, J=8 Hz, 1H); 7.78 (s, 1H); 7.30 (d, J=4 Hz, 1H); 7.18 (dd, J=4,8 Hz, 1H); 3.72 (s, 3H); 3.42 (m, 1H); 3.40 (s, 6H); 3.10 (m, 1H); 2.32 (m, 2H): 2.02 (m, 1H); 1.73 (m, 2H); 1.55 (m, 1H); 1.33 (s, 3H); 1.13 (m, 1H) and 1.04 (s, 3H).

MS: m/e 472 (M+).

EXAMPLE 33

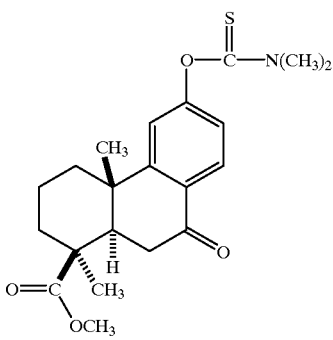

To a solution of 1.5 g (4.96 mmol) of the compound of Example 21 and 278 mg (4.96 mmol) of potassium hydroxide (KOH) in 50 ml of $H_2O$, was added 817 mg (6.6 mmol) of dimethylthiocarbamoyl chloride. The reaction mixture was stirred rapidly for 15 minutes, then diluted with 100 ml of $Et_2O$ and the organic phase was separated, dried over $Na_2SO_4$, filtered and concentrated in vacuo to provide an oily solid. This solid was triturated in MeOH and then isolated by filtration.

Yield: 1.45 g (75%).

$^1$H NMR (300 MHz, $CDCl_3$): δ8.10 (d, J=8 Hz, 1H); 7.13 (d, J=4 Hz, 1H); 7.0 (dd, J=4,8 Hz, 1H); 3.73 (s, 3H); 3.44 (s, 3H); 3.33 (s, 3H); 3.22 (m, 1H); 2.98 (m, 1H); 2.30 (m, 2H); 2.05 (m, 2H); 1.62 (m, 2H); 1.28 (s, 3H); 1.17 (m, 1H) and 1.14 (s, 3H).

MS: m/e 389 (M+).

EXAMPLE 34

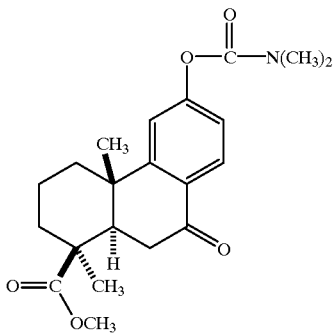

The compound was prepared by melting 300 mg (0.77 mmol) of the compound of Example 33 in a flask under nitrogen ($N_2$). The liquified residue was cooled to provide 300 mg of a glassy solid (quantitative)

$^1$H NMR (300 MHz, $CDCl_3$): δ8.02 (d, J=8 Hz, 1H); 7.58 (d, J=4 Hz, 1H); 7.42 (dd, J=4, 8 Hz, 1H); 3.70 (s, 3H); 3.22 (m, 1H); 3.04 (m, 7H); 2.35 (m, 2H); 2.05 (m, 2H); 1.70 (m, 1H); 1.57 (m, 1H); 1.27 (s, 3H); 1.16 (s, 3H) and 1.14 (m, 1H).

MS: m/e 390 (M+).

EXAMPLE 35

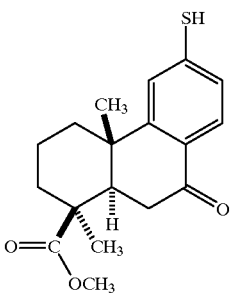

To a solution of 480 mg (1.23 mmol) of the compound of Example 34 in 15.0 ml of MeOH, was added 689 mg (12.3 mmol) of KOH. The reaction mixture was refluxed for 20 minutes, cooled to room temperature, and diluted with 80 ml of $H_2O$ and 100 ml of $Et_2O$. The resulting layers were separated and the aqueous layer was acidified with 4.0 ml of 5N HCl and then combined with 100 ml of $CH_2Cl_2$. The resultant layers were separated and the organic layer was dried over $Na_2SO_4$, filtered and concentrated in vacuo.

Yield: 370 mg of a tan solid (94%).

$^1$H NMR (300 MHz, $CDCl_3$): δ7.90 (d, J=8 Hz, 1H); 7.24 (d, J=4 Hz, 1H); 7.15 (d, J=8 Hz, 1H); 3.70 (s, 3H); 3.60 (s, 1H); 3.18 (m, 1H); 2.95 (m, 1H); 2.32 (m, 2H); 2.02 (m, 2H); 1.72 (m, 1H); 1.50 (m, 1H); 1.25 (s, 3H); 1.14 (m, 1H) and 1.10 (s, 3H).

MS: m/e 318 (M+).

EXAMPLE 36

A.

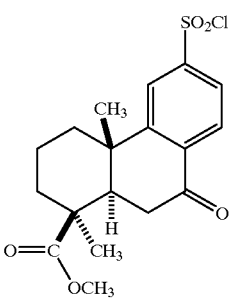

To a 0° C. solution of 320 mg (1.01 mmol) of the compound of Example 35 in 20.0 ml of $CH_3CN$ was added 253 mg (2.5 mmol) of potassium nitrate ($KNO_3$) and 0.201 ml (2.5 mmol) of sulfuryl chloride. The reaction mixture was stirred for 30 minutes at 0° C., diluted with 100 ml of $Et_2O$ and washed with 30 ml of $H_2O$. The organic phase was separated, dried over $Na_2SO_4$, filtered and concentrated in vacuo to provide 280 mg of a crude yellow solid. This solid was purified using radial chromatography (1000 micron plate, eluent of 2% EtOAc in $CH_2Cl_2$).

Yield: 105 mg (27%).

$^1$H NMR (300 MHz, $CDCl_3$): δ8.23 (d, J=8 Hz, 1H); 8.08 (d, J=4 Hz, 1H); 7.93 (dd, J=4,8 Hz, 1H); 3.74 (s, 3H); 3.33 (m, 1H); 3.10 (m, 1H); 2.40 (m, 2H); 2.03 (m, 2H); 1.75 (m, 1H) 1.55 (m, 1H); 1.28 (s, 3H); 1.18 (s, 3H) and 1.16 (m, 1H).

MS: m/e 385 (M+).

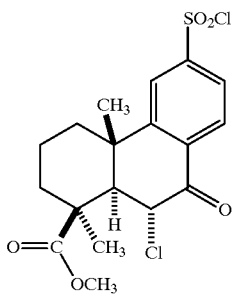

The compound was isolated from the reaction mixture detailed in Example 36A.

Yield: 135 mg.

$^1$H NMR (300 MHz, CDCl$_3$): δ8.02 (m, 3H); 5.8 (d, J=8 Hz, 1H); 3.75 (s, 3H); 2.35 (m, 3H); 1.85 (m, 3H); 1.53 (m, 1H); 1.50 (s, 3H) and 0.96 (s, 3H).

MS: m/e 418 (M+).

EXAMPLE 37

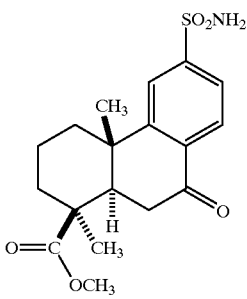

To a solution of 100 mg (0.26 mmol) of the compound of Example 36A in 1.0 ml of THF, was added 60 41 (0.84 mmol) of concentrated NH$_4$OH. The reaction mixture was diluted with 20.0 ml CH$_2$Cl$_2$, washed with 10.0 ml H$_2$O, dried over Na$_2$SO$_4$, filtered and concentrated in vacuo.

Yield: 90 mg (95%).

$^1$H NMR (300MHz, CDCl$_3$): δ8.13 (d, J=8 Hz, 1H); 8.0 (d, J=4 Hz, 1H); 7.80 (dd, J=4,8 Hz, 1H); 5.01 (s, 2H); 3.73 (s, 3H); 3.27 (m, 1H); 3.02 (m, 1H); 2.38 (m, 2H); 2.02 (m, 2H); 1.73 (m, 1H); 1.54 (m, 1H); 1.27 (s, 3H); 1.17 (m, 1H) and 1.13 (s, 3H).

EXAMPLE 38

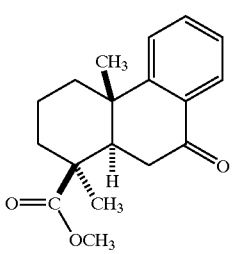

To a solution of 50 mg (0.157 mmol) of the compound of Example 35 in 15.0 ml of EtOH, was added 100 mg of Rainey nickel catalyst. The reaction mixture was shaken under hydrogen gas (60 psi) at room temperature for 3 hours and then filtered and concentrated in vacuo. The crude material was purified using radial chromatography (1000 micron plate, gradient eluent of 1–10% EtOAc in CH$_2$Cl$_2$).

Yield: 15 mg (33%).

$^1$H NMR (300 MHz, CDCl$_3$): δ8.03 (d, J=8 Hz, 1H); 7.54 (t, J=8 Hz, 1H); 7.40 (d, J=8 Hz, 1H); 7.31 (d, J=8 Hz, 1H); 3.72 (s, 3H); 3.22 (m, 1H); 3.0 (m, 1H); 2.37 (m, 2H); 2.03 (m, 2H); 1.73 (m, 1H); 1.55 (m, 1H); 1.26 (s, 3H); 1.14 (m, 1H) and 1.12 (s, 3H).

MS: m/e 286 (M+).

EXAMPLE 39

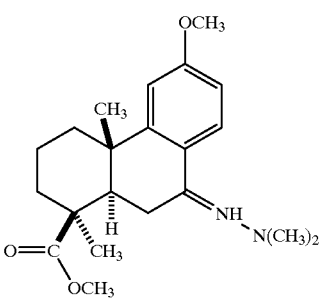

To a solution of 200 mg (0.632 mmol) of the compound of Example 6 in 2.5 ml of EtOH was added 43 μl (0.75 mmol) of AcOH, and 396 μl (5.2 mmol) of 1,1-dimethylhydrazine. The reaction mixture was heated to 80° C., reacted for 4 hours, concentrated in vacuo, diluted with Et$_2$O, washed with H$_2$O, dried over Na$_2$SO$_4$, filtered and then concentrated in vacuo to provide an oil. This oil was purified using radial chromatography (2000 micron plate, eluent of 8% EtOAc in CH$_2$Cl$_2$).

Yield: 145 mg (64%).

$^1$H NMR (300 MHz, CDCl$_3$): δ8.13 (d, J=8 Hz, 1H); 6.81 (d, J=4 Hz, 1H); 6.74 (dd, J=4,8 Hz, 1H); 3.81 (s, 3H); 3.71 (s, 3H); 3.61 (m, 1H); 2.78 (m, 1H); 2.60 (s, 6H); 2.28 (m, 2H); 1.72 (m, 2H); 1.47 (m, 1H); 1.32 (s, 3H); 1.12 (m, 1H) and 1.06 (s, 3H).

MS: m/e 358 (M+).

Elemental Analysis for C$_{21}$H$_{30}$N$_2$O$_3$: Calcd: C, 70.36; H, 8.44; N, 7.81; Found: C, 70.30; H, 7.91; N, 8.00.

EXAMPLE 40

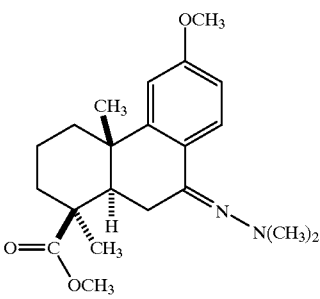

To a solution of 98 mg (0.273 mmol) of the compound from Example 39 in 2.0 ml of Et$_2$O, was added 0.273 ml of a solution containing 1.0 ml of concentrated HCl in 11.0 ml of CH$_3$CN. The reaction mixture was diluted with 10.0 ml of CH₃CN and then concentrated in vacuo to provide an oily residue which was triturated with 3.0 ml of Et₂O and then isolated by filtration.

Yield: 105 mg (97%).

¹H NMR (300 MHz, d₆-DMSO): δ8.35 (bs, 1H); 8.10 (d, J=8 Hz, 1H); 6.80 (d, J=4 Hz, 1H); 6.71 (dd, J=4, 8 Hz, 1H); 3.78 (s, 3H); 3.68 (s, 3H); 3.57 (m, 1H); 2.74 (m, 1H); 2.58 (s, 6H); 2.26 (m, 2H); 1.70 (m, 2H); 1.45 (m, 1H); 1.30 (s, 3H); 1.10 (m, 1H) and 1.02 (s, 3H).

MS: m/e 358 (M+-HCl).

Elemental Analysis for C₂₁H₃₁N₂O₃Cl: Calc: C, 63.87; H, 7.91; N, 7.09; Cl, 8.98; Found: C, 64.17; H, 8.07; N, 7.07; Cl, 9.08.

EXAMPLE 41

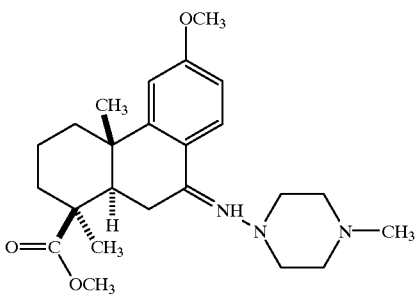

To a solution of 2.0 g (6.32 mmol) of the compound from Example 6 in 20.0 ml of EtOH, was added 12.0 ml (100 mmol) of 1-amino-4-methylpiperazine, 2.8 g (50 mmol) of KOH. The mixture was heated to 80° C. for 2 hours, concentrated in vacuo, diluted with 250 ml of Et₂O, and washed with 100 ml of H₂O. The resultant layers were separated and the organic layer was dried over Na₂SO₄, filtered and concentrated in vacuo to provide a thick oil which was purified using radial chromatography (4000 micron plate, gradient eluent of 0–15% MeOH in EtOAc).

Yield: 2.29 g (88%).

¹H NMR (300 MHz, CDCl₃): δ8.13 (d, J=8 Hz, 1H); 6.80 (d, J=4 Hz, 1H); 6.72 (dd, J=4,8 Hz, 1H); 3.80 (s, 3H); 3.70 (s, 3H); 3.66 (m, 1H); 2.95 (m, 2H); 2.80 (m, 2H); 2.70 (m, 1H); 2.60 (m, 4H); 2.35 (s, 3H); 2.26 (m, 2H); 1.95 (m, 1H); 1.70 (m, 2H); 1.45 (m, 1H); 1.30 (s, 3H); 1.10 (m, 1H) and 1.03 (s, 3H).

EXAMPLE 42

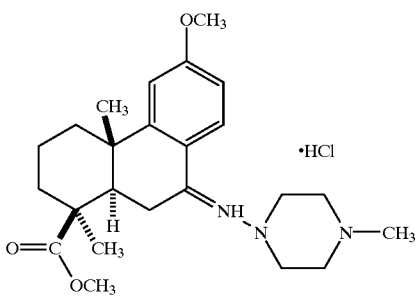

The compound was prepared substantially in accordance with the procedure detailed in Example 40, using 2.29 g (5.54 mmol) of the compound of Example 41, and 5.54 ml of a solution consisting of 1.0 ml concentrated HCl and 11.0 ml of CH₃CN.

Yield: 2.31 g (93%).

¹H NMR (300 MHz, d₆-DMSO): 510.5 (bs, 1H); 8.02 (d, J=8 Hz, 1H); 6.88 (d, J=4 Hz, 1H); 6.80 (dd, J=4,8 Hz, 1H); 3.78 (s, 3H); 3.64 (s, 3H); 3.50 (m, 1H); 3.33 (m, 4H); 3.03 (m, 4H); 2.63 (m, 1H); 2.77 (s, 3H); 2.30 (m, 1H); 2.10 (m, 1H); 1.84 (m, 1H); 1.68 (m, 1H); 1.58 (m, 1H); 1.31 (m, 1H); 1.20 (s, 3H); 1.10 (m, 1H) and 0.93 (s, 3H).

MS: m/e 413 (M+-HCl).

Elemental Analysis for C₂₄H₃₆N₃O₃Cl: Calcd: C, 64.05; H, 8.06; N, 9.34; Cl, 7.21; Found: C, 63.85; H, 7.98; N, 9.50; Cl, 7.67.

EXAMPLE 43

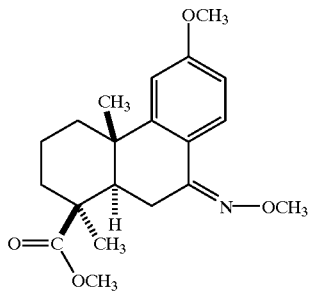

To a solution of 330 mg (1.04 mmol) of the compound from Example 6 in 4.0 ml of EtOH was added 100 mg (1.2 mmol) of methoxyamine hydrochloride and 98 mg (1.2 mmol) of NaOAc. The reaction mixture was stirred at room temperature for 67 hours, heated to 80° C., reacted for 3 hours and then concentrated in vacuo. The crude material was purified using radial chromatography (2000 micron plate, eluent of 3% EtOAc in CH₂Cl₂) to provide an oil which was dissolved in MeOH and recrystallized at 0° C.

Yield: 43 mg (12%).

¹H NMR (300 MHz, CDCl₃): δ7.95 (d, J=8 Hz, 1H); 6.83 (d, J=4 Hz, 1H); 6.75 (dd, J=4,8 Hz, 1H); 4.0 (s, 3H); 3.82 (s, 3H); 3.72 (s, 3H); 3.32 (m, 1H); 2.97 (m, 1H); 2.28 (m, 2H); 1.98 (m, 1H); 1.68 (m, 2H); 1.52 (m, 1H); 1.25 (s, 3H); 1.10 (m, 1H) and 0.98 (s, 3H).

MS: m/e 345 (M+).

EXAMPLE 44

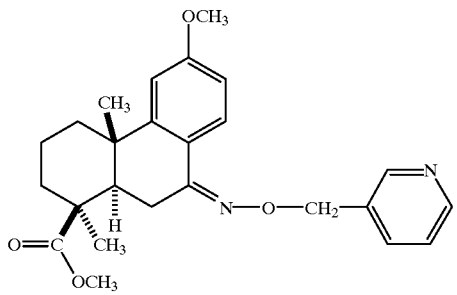

To a solution of 175 mg (0.528 mmol) of the compound from Example 7 in 3.0 ml of dioxane, was added 235 mg (1.70 mmol) of K₂CO₃ and 112 mg (0.687 mmol) of 3-picolyl chloride hydrochloride. The reaction mixture was heated to 100° C., reacted for 15 minutes and then concentrated in vacuo to provide a tan residue. This residue was dissolved in 75.0 ml of EtOAc, washed with a saturated NaHCO₃ solution, dried over Na₂SO₄, filtered and then concentrated in vacuo to provide 180 mg of crude material which was purified using radial chromatography (2000 micron plate, gradient eluent of 5–20% EtOAc in CH₂Cl₂).

Yield: 90 mg (40%).

$^1$H NMR (300 MHz, CDCl₃): δ8.70 (m, 1H); 8.55 (m, 1H); 7.9 (d, J=8 Hz, 1H); 7.77 (m, 1H); 7.30 (m, 1H); 6.80 (d, J=4 Hz, 1H); 6.72 (dd, J=4,8 Hz, 1H); 5.22 (s, 2H); 3.80 (s, 3H); 3.70 (s, 3H); 3.37 (m, 1H); 3.02 (m, 1H); 2.25 (m, 2H); 1.95 (m, 1H); 1.67 (m, 2H); 1.50 (m, 1H); 1.27 (s, 3H); 1.10 (m, 1H) and 0.97 (s, 3H).

EXAMPLE 45

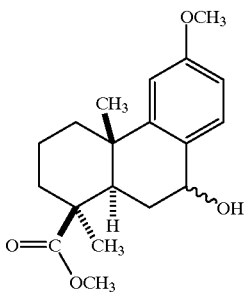

To a solution of 500 mg (1.58 mmol) of the compound from Example 6 in 5.0 ml of MeOH was added 101 mg (1.6 mmol) of sodium cyanoborohydride and a trace (a trace) of methyl orange. A 2N HCl methanolic solution was added dropwise to maintain the red color of the reaction. After 15 minutes, the color stabilized (red) and the reaction was stirred for 45 minutes longer. The reaction mixture was concentrated in vacuo to provide an orange residue. The residue was dissolved in Et₂O and washed with brine, dried over Na₂SO₄, filtered and concentrated in vacuo to provide an oil which solidified on standing. The solid was purified using radial chromatography (4000 micron plate, eluent of 5% EtOAc in CH₂Cl₂).

Yield: 226 mg (45%).

$^1$H NMR (300 MHz, CDCl₃): δ7.50 (d, J=8 Hz, 1H); 6.77 (m, 2H); 4.68 (m, 1H); 3.80 (s, 3H); 3.62 (s, 3H); 2.55 (m, 1H); 2.22 (m, 2H); 1.90 (m, 3H); 1.58 (m, 2H); 1.35 (m, 1H); 1.27 (s, 3H); 1.03 (m, 1H) and 1.0 (s, 3H).

MS: m/e 318 (M+).

EXAMPLE 46

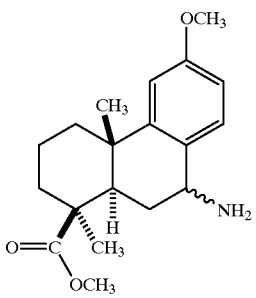

To a solution of 1.0 g (3.16 mmol) of the compound from Example 6 in 15.0 ml of MeOH, was added 1.0 g crushed and activated 4.0 Å molecular sieves, 2.46 g (32 mmol) of ammonium acetate and 201 mg (3.2 mmol) of sodium cyanoborohydride. The reaction was stirred at room temperature for 1 hour and then quenched with 30.0 ml of H₂O. The desired compounds were extracted with 100 ml of Et₂O, washed with a saturated NaHCO₃ solution, dried over Na₂SO₄, filtered and then concentrated in vacuo to provide a yellow residue. This residue was purified using flash chromatography (SiO₂, gradient eluent of 0–5% EtOAc in CH₂Cl₂).

Yield: 290 mg (29%).

$^1$H NMR (300 MHz, CDCl₃): δ7.45 (d, J=8 Hz, 1H); 6.78 (m, 2H); 3.85 (m, 1H); 3.78 (s, 3H); 3.67 (s, 3H); 2.40 (m, 1H); 2.22 (m, 2H); 1.95 (m, 2H); 1.78 (m, 1H); 1.58 (m, 3H); 1.40 (m, 1H); 1.27 (s, 3H); 1.10 (m, 1H) and 1.05 (s, 3H).

EXAMPLE 47

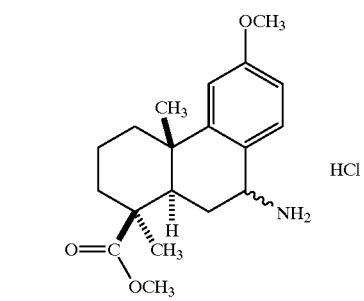

To a solution of 20 mg (0.063 mmol) of the compound from Example 46 in 3.0 ml of a 2:1 Et₂O/hexane mixture, was added 63 μl of a solution consisting of 1.0 ml of concentrated HCl in 11.0 ml of CH₃CN. The resultant precipitate was filtered, washed with 3.0 ml of a 1:1 Et₂O/hexane mixture and dried in vacuo.

Yield: 21 mg (95%).

$^1$H NMR (300 MHz, d₆-DMSO): δ8.42 (m, 3H); 7.50 (d, J=8 Hz, 1H); 6.82 (m, 2H); 4.35 (m, 1H); 3.70 (s, 3H); 3.58 (s, 3H); 2.50 (m, 1H); 2.20 (m, 2H); 1.87 (m, 2H); 1.58 (m, 2H); 1.25 (m, 1H); 1.20 (s, 3H); 1.10 (m, 1H) and 1.0 (s, 3H).

MS: m/e 317 (M+).

EXAMPLE 48

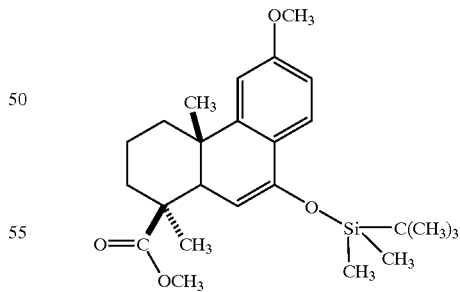

To a solution of 1.0 g (3.16 mmol) of the compound from Example 6 in 15.0 ml of CH₂Cl₂, was added 0.44 ml (3.8 mmol) of 2,6-lutidine and 0.80 ml (3.5 mmol) of t-butyldimethylsilyl trifluoromethanesulfonate. The reaction mixture was stirred at room temperature for 1 hour, diluted with Et₂O and washed sequentially with H₂O and a saturated NaHCO₃ solution, dried over Na₂SO₄, filtered and concentrated in vacuo.

Yield: 1.36 g (quantitative).

¹H NMR (300 MHz, CDCl₃): δ7.42 (d, J=8 Hz, 1H); 6.78 (d, J=4 Hz, 1H); 6.72 (dd, J=4,8 Hz, 1H); 5.55 (d, J=4 Hz, 1H); 3.80 (s, 3H); 3.68 (s, 3H); 2.42 (d, J=4 Hz, 1H); 2.30 (m, 1H); 2.15 (m, 1H); 1.95 (m, 1H); 1.65 (m, 2H); 1.27 (s, 3H); 1.10 (m, 1H); 1.03 (s, 9H); 0.90 (s, 3H); 0.28 (s, 3H) and 0.18 (s, 3H).

EXAMPLE 49

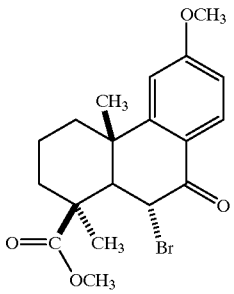

To a solution of 1.36 g (3.16 mmol) of the compound from Example 48 in 10.0 ml of THF, was added 1.6 ml of a 1M bromine in AcOH solution. The reaction mixture was diluted with Et₂O, washed with a saturated NaHCO₃ solution, dried over Na₂SO₄, filtered and then concentrated in vacuo to provide a yellow solid. This solid was dissolved in 10.0 ml of MeOH, cooled to 0° C. and reacted for 18 hours. The resultant white crystals were filtered and dried in vacuo.

Yield: 935 mg (75%).

¹H NMR (300 MHz, CDCl₃): δ7.82 (d, J=8 Hz, 1H); 6.88 (dd, J=4,8 Hz, 1H); 6.83 (d, J=8 Hz, 1H); 5.82 (d, J=6 Hz, 1H); 3.86 (s, 3H); 3.73 (s, 3H); 2.52 (d, J=6 Hz, 1H); 2.37 (m, 1H); 2.17 (m, 1H); 1.92 (m, 1H); 1.78 (m, 2H); 1.57 (s, 3H); 1.22 (m, 1H) and 0.87 (s, 3H).

EXAMPLE 50

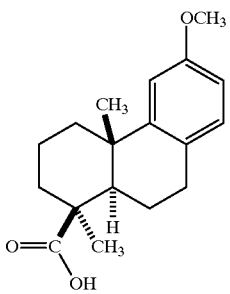

To a solution of 1.0 g (3.31 mmol) of the compound from Example 1A in 10.0 ml of THF, was added 1.0 g (6.4 mmol) of benzeneselenol, 302 mg (6.29 mmol) of a 50% dispersion of NaH in mineral oil and 84 mg (0.32 mmol) of 18-crown-6 ether. The reaction mixture was refluxed for 15 hours, cooled to room temperature and diluted with 100 ml of Et₂O and 20 ml of 1N HCl. The resultant layers were separated and the organic layer was dried over Na₂SO₄, filtered and concentrated in vacuo. The crude material was purified using flash chromatography (SiO₂, eluent of 25% EtOAc in hexane) to provide a solid which was recrystallized from Et₂O/hexane.

Yield: 731 mg (77%).

¹H NMR (300 MHz, CD₃OD): δ6.9 (d, J=8 Hz, 1H); 6.75 (d, J=4 Hz, 1H); 6.60 (dd, J=4,8 Hz, 1H); 3.70 (s, 3H); 2.70 (m, 2H); 2.20 (m, 3H); 2.20 (m, 2H); 1.53 (m, 2H); 1.33 (m, 1H); 1.27 (s, 3H); 1.10 (s, 3H) and 1.07 (m, 1H).

MS: m/e 288 (M+).

EXAMPLE 51

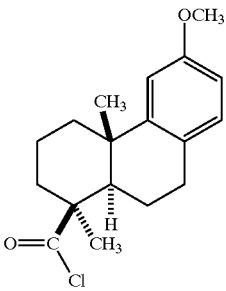

To a solution of 360 mg (1.25 mmol) of the compound from Example 50 in 25.0 ml of toluene, was added 0.545 ml (6.25 mmol) of oxalyl chloride in 25 μl of DMF. The reaction mixture was stirred at room temperature with gas evolution for 30 minutes, heated briefly (2 minutes) to reflux and then concentrated in vacuo.

Yield: 381 mg crystals (99%).

¹H NMR (300 MHz, CDCl₃): δ6.98 (d, J=8 Hz, 1H); 6.82 (d, J=4 Hz, 1H); 6.68 (dd, J=4,8 Hz, 1H); 3.80 (s, 3H); 2.80 (m, 2H); 2.25 (m, 3H); 2.05 (m, 2H); 1.65 (m, 2H); 1.42 (m, 1H); 1.40 (s, 3H); 1.25 (s, 3H) and 1.20 (m, 1H).

EXAMPLE 52

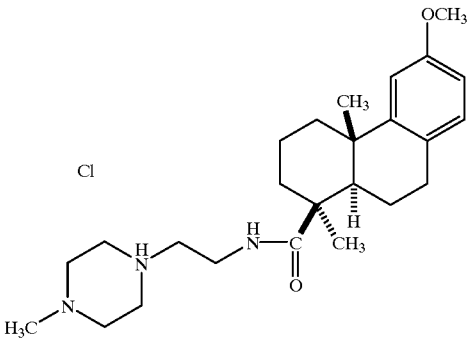

To a solution of 100 mg (0.33 mmol) of the compound from Example 51 in 2.0 ml of CH₂Cl₂, were added 43 μl (0.358 mmol) of 2-(2-aminoethyl)pyridine, 50 μl (0.36 mmol) of Et₃N and 5 mg (0.036 mmol) of 4-dimethylaminopyridine in 4.0 ml of CH₂Cl₂. The reaction mixture was diluted with CH₂Cl₂, washed with H₂O, dried over Na₂SO₄, filtered and concentrated in vacuo to provide a tan solid. This solid was dissolved in 3.0 ml of CH₃CN and treated with 0.36 ml of a solution of 1.0 ml of concentrated HCl in 11.0 ml of CH₃CN.

Yield: 120 mg (78%).

¹H NMR (300 MHz, d₆-DMSO): δ8.75 (d, J=6 Hz, 1H); 8.40 (t, J=6 Hz, 1H); 7.80 (m, 2H); 7.40 (m, 1H); 6.85 (d, J=8 Hz, 1H); 6.70 (d, J=4 Hz, 1H); 6.60 (dd, J=4, 8 Hz, 1H); 3.60 (s, 3H); 3.55 (m, 2H); 3.19 (m, 2H); 2.68 (m, 1H); 2.55 (m, 1H); 2.10 (m, 3H); 1.78 (m, 2H); 1.43 (m, 1H); 1.30 (m, 1H); 1.17 (m, 1H); 1.02 (s, 3H); 0.99 (m, 1H) and 0.80 (s, 3H).

MS: m/e 392 (M+-HCl).

As noted above, the compounds of the present invention are useful for inhibiting an envelope virus that undergoes hemagglutinin-mediated fusion with a host cell. Thus, the claimed compounds may be used to treat or prevent a viral infection where the virus is an envelope virus that undergoes hemagglutinin-mediated fusion which comprises administering to an virus-infected cell, a cell susceptible to infection or a mammal in need thereof an effective amount of a compound of formula I or a pharmaceutically acceptable salt thereof. The claimed compounds may also be used to inhibit viral replication in an envelope virus that undergoes hemagglutinin-mediated fusion which comprises administering to a virus-infected cell, a cell susceptible to infection or a mammal in need thereof, an effective amount of a compound of formula I or a pharmaceutically acceptable salt thereof.

The term "effective amount" as used herein, means an amount of a compound of the present invention which is capable of inhibiting the hemagglutinin mediated fusion of the virus with the host cell. The inhibition contemplated by the present method includes both therapeutic and prophylactic treatment, as appropriate. The specific dose of compound administered according to this invention to obtain therapeutic and/or prophylactic effects will, of course, be determined by the particular circumstances surrounding the case, including, for example, the compound administered, the route of administration, the condition being treated and the individual being treated. A typical daily dose (administered in single or divided doses) will contain a dosage level of from about 0.01 mg/kg to about 50 mg/kg of body weight of an active compound of this invention. Preferred daily doses generally will be from about 0.05 mg/kg to about 20 mg/kg and ideally from about 0.1 mg/kg to about 10 mg/kg.

The compounds can be administered by a variety of routes including oral, rectal, transdermal, subcutaneous, intravenous, intramuscular and intranasal. The compounds of the present invention are preferably formulated prior to administration. Therefore, another embodiment of the present invention is a pharmaceutical formulation comprising an effective amount of a compound of formula I or a pharmaceutically acceptable salt thereof and a pharmaceutically acceptable carrier, diluent or excipient therefor.

The active ingredient in such formulations comprises from 0.1% to 99.9% by weight of the formulation. By "pharmaceutically acceptable" it is meant that the carrier, diluent or excipient is compatible with the other ingredients of the formulation and not deleterious to the recipient thereof.

The present pharmaceutical formulations are prepared by known procedures using known and readily available ingredients. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), ointments containing, for example, up to 10% by weight of the active compound, soft and hard gelatin capsules, suppositories, sterile injectable solutions, sterile packaged powders and the like.

The following experiments were carried out to demonstrate the ability of the compounds of the present invention to inhibit influenza.

In vitro CPE/XTT Assay

MDCK cells were dispersed in a microtiter plate (96 wells) at 10,000 cells per well with Medium 199 containing Earl's balanced salt solution (EBSS), 1% fetal bovine serum (FBS), penicillin (100 units/ml) and streptomycin (100 µg/ml). After standing overnight at 37° C. in a carbon dioxide ($CO_2$) incubator, the MDCK cells were infected with ~0.1 moi (mutiplicity of infection) of influenza virus (i.e. A/Kawasaki/89 or B/Hong Kong and B/Great Lakes) at 0.03 mol. After allowing the virus to adsorb to the cells for 1–2 hours, medium containing serial dilutions of drug or medium alone was added to the wells. The resultant mixtures were incubated for 2–3 days (until extensive cpe was apparent in medium alone wells). The antiviral effect of a test compound was assessed by performing the following XTT assay.

A fresh solution (0.4 mg/ml) of XTT [2,3-bis(methoxy-4-nitro-5-sulfophenyl)-2H-tetraazolium-5-carboxanilide, inner salt, sodium salt] in warm medium without FBS was prepared. For each 5 ml of the XTT solution, 25 µl of 5mM PMS (phenazine methosulfate) in phosphate buffer saline was added. After withdrawing the cultured supernatant, 100 µl of the freshly prepared XTT/PMS mixture was added to each of the microliter wells. The wells were then incubated at 37° C. (under $CO_2$) for 3–4 hours or until color change is prominent. The absorbance at 450 nm (ref. 650 nm) was read in a spectrophotometer. The concentration of test compound required to cause 50% cytotoxic effect ($TC_{50}$) relative to a control with no drug and no virus present and which inhibits the development of virus cytopathic effect (cpe) by 50% ($IC_{50}$) or 90% ($IC_{90}$) was determined from the linear portion of each dose response curve.

Using this CPE/XTT assay, the $IC_{50}$ of the compounds of formula I was determined to be in the range of 0.005–100.0 µg/ml for influenza A/Kawasaki/89 and in the range of 0.37–100 µg/ml for influenza B/Great Lakes.

Plaque Reduction Assay

Susceptible MDCK cells were grown in 6 well tissue culture treated cluster plates at $1 \times 10^6$ cells/well in Minimum 199 with 1 percent fetal bovine serum, penicillin (100 units/ml) and streptomycin (100 µg/ml). After overnight incubation at 37° C., the growth medium was removed and 0.2 ml/well of an appropriate dilution of virus was added. After adsorption for 1–2 hour at room temperature, the infected cell sheet was overlaid with equal parts of 1.5% sterile agarose solution and a twofold concentration of medium 199 (with 2% fetal bovine serum, 100 units/ml of penicillin and 100 µg/ml streptomycin) containing varying concentrations of compounds.

The compounds were dissolved in DMSO at a concentration of 20 mg/ml and an aliquot was diluted to the desired concentration in DMSO and then added to the agar medium mixture. The plates were incubated in a $CO_2$ incubator at 37° C. until the DMSO control wells contained plaques of optimal size. Then, a solution containing 10 percent formalin and 2 percent sodium acetate was added to each well to inactivate the virus and fix the cell sheet to the plastic surface. The fixed cell sheets were stained with 0.5 percent crystal violet and the plaques were counted. Results from duplicate wells at each concentration were averaged and compared with DMSO control wells. The inhibition of plaque formation by 50 or 90 percent ($IC_{50}$ or $IC_{90}$) was calculated from the linear region of the inhibition concentration curve using the method of Reed and Muench, Am. J. Hyg., vol. 27, pages 493–497 (1958).

Using this plaque reduction assay, the $IC_{50}$ of the compounds of formula I with influenza A/Kawasaki was determined to be in the range of 0.006 μg/ml to 32 μg/ml.

What is claimed is:

1. A compound of the formula

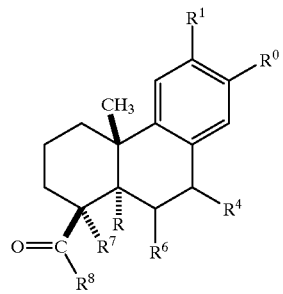

I wherein:

R is hydrogen;

$R^0$ is hydrogen, hydroxy, $C_1$–$C_6$ alkyl, $C_1$–$C_6$ alkoxy, hydroxy($C_1$–$C_6$ alkyl), sulfhydryl, sulfamyl, —$SO_2$—Cl, —S—C(O)—N(CH$_3$)$_2$, amino, $C_1$–$C_4$ alkylamino, di($C_1$–$C_4$ alkyl)amino, $C_1$–$C_4$ alkylsulfonylamino, di($C_1$–$C_4$ alkylsulfonyl)amino, —$X^0$—O—C(O)—$C_1$–$C_4$ alkyl, —O—($X^1$)$_i$, —C(O)—$X^3$, —N—C(O)—$R^2$ or —O—$R^3$;

$R^1$ is hydrogen, $C_1$–$C_6$ alkyl, hydroxy($C_1$–$C_6$ alkyl), sulfhydryl, sulfamyl, —$SO_2$—Cl, —S—C(O)—N(CH$_3$)$_2$, amino, $C_1$–$C_4$ alkylamino, di($C_1$–$C_4$ alkyl)amino, $C_1$–$C_4$ alkylsulfonylamino, di($C_1$–$C_4$ alkylsulfonyl)amino, —($C_1$–$C_6$ alkyl) —O—C(O)—$C_1$–$C_4$ alkyl, —O—($X^1$)$_i$, —C(O)—$X^3$, —N—C(O)—$R^2$ or —O—$R^3$;

$X^0$ is a bond or divalent($C_1$–$C_6$ alkyl);

$X^1$ is an amino acid ester of glycine, alanine or valine;

i is 1, 2 or 3;

$X^3$ is $C_1$–$C_6$ alkyl, $C_1$–$C_6$ alkoxy, halo($C_1$–$C_6$ alkyl), hydroxy($C_1$–$C_6$ alkyl) or phenyl;

$R^2$ is $C_1$–$C_4$ alkyl, $C_1$–$C_4$ alkoxy, halo($C_1$–$C_4$ alkyl), hydroxy($C_1$–$C_4$ alkyl), phenyl, p-methoxy-phenyl, p-fluoro-phenyl, naphthyl, or cyclohexyl;

$R^3$ is $C_2$–$C_6$ alkenyl, —$CH_2$—$R^{3a}$, —C(O)—$R^{3b}$, —C(S)—$R^{3c}$, —C(CH$_3$)$_2$C(O)NH$_2$, phenyl or a group of the formula

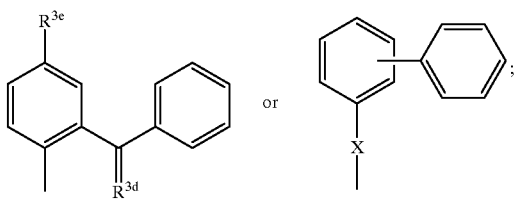

$R^{3a}$ is phenyl, p-fluorophenyl, cyclohexyl, cyclopentyl, cyclopropyl or naphthyl;

$R^{3b}$ is benzyloxy, $C_1$–$C_6$ alkoxy, halo($C_1$–$C_4$ alkoxy), amino, $C_1$–$C_4$ alkylamino or di($C_1$–$C_4$ alkyl)amino;

$R^{3c}$ is amino, $C_1$–$C_4$ alkylamino or di($C_1$–$C_4$ alkyl)amino;

$R^{3d}$ is oxygen, hydroximino, hydrazino or =CHZ;

Z is hydrogen, $C_1$–$C_4$ alkyl, halogen, di($C_1$–$C_4$ alkyl)amino, $C_1$–$C_4$ alkoxycarbonyl, carbamoyl($C_1$–$C_4$ alkyl), N-($C_1$–$C_4$ alkyl)carbamoyl or N,N-di($C_1$–$C_4$ alkyl)carbamoyl;

$R^{3e}$ is hydrogen, or trifluoromethyl;

X is a bond or —(CH$_2$)—;

$R^4$ is =N—$R^5$;

$R^5$ is hydroxy, amino, $C_1$–$C_4$ alkylamino, di($C_1$–$C_4$ alkyl)amino, $C_1$–$C_4$ alkoxy, benzyloxy, or —O—CH$_2$—C(O)—$R^{5a}$;

$R^{5a}$ is hydroxy or $C_1$–$C_4$ alkoxy;

$R^6$ is hydrogen, halo, $C_1$–$C_4$ alkyl or =O;

$R^7$ is hydrogen or $C_1$–$C_4$ alkyl;

$R^8$ is hydroxy, or $C_1$–$C_6$ alkoxy;

or a pharmaceutically acceptable salt thereof.

2. The compound of claim 1 wherein $R^0$ is hydrogen, hydroxy, $C_1$–$C_6$ alkyl, $C_1$–$C_6$ alkoxy, hydroxy($C_1$–$C_6$ alkyl), —$X^0$—O—C(O)—$C_1$–$C_4$ alkyl, —O—($X^1$)$_i$, —C(O)—$X^3$ or —O—$R^3$;

$R^1$ is hydrogen, sulfhydryl, sulfamyl, —$SO_2$—Cl, amino, di($C_1$–$C_4$ alkylsulfonyl)amino —C(O)—$X^3$, —N—C(O)—$R^2$ or —O—$R^3$;

$X^0$ is a bond or divalent($C_1$–$C_6$ alkyl);

$X^1$ is an amino acid ester of glycine, alanine or valine;

i is 1 or 2;

$X^3$ is $C_1$–$C_6$ alkyl;

$R^2$ is hydroxy($C_1$–$C_4$ alkyl);

$R^3$ is $C_2$–$C_6$ alkenyl, —$CH_2$—$R^{3a}$, —C(O)—$R^{3b}$, —C(S)—$R^{3c}$, —C(CH$_3$)$_2$C(O)NH$_2$ or a group of the formula:

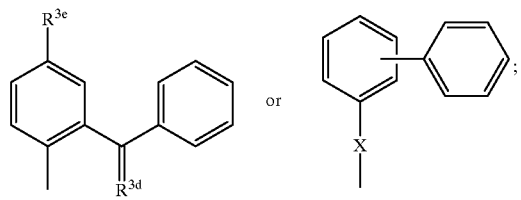

$R^{3a}$ is phenyl, or p-fluorophenyl;

$R^{3b}$ is halo($C_1$–$C_4$ alkoxy) or di($C_1$–$C_4$ alkyl)amino;

$R^{3c}$ is di($C_1$–$C_4$ alkyl)amino;

$R^{3d}$ is oxygen or hydroximino;

$R^{3e}$ is hydrogen, nitro or trifluoromethyl;

X is a bond;

$R^4$ is =N—$R^5$;

$R^5$ is hydroxy, amino, di($C_1$–$C_4$ alkyl)amino, $C_1$–$C_4$ alkoxy, or —O—CH$_2$—C(O)—$R^{5a}$;

$R^6$ is hydrogen, chloro, bromo, methyl or =O;

$R^7$ is hydrogen or methyl;

$R^8$ is hydroxy, chloro, or methoxy;

or a pharmaceutically acceptable salt thereof.

3. The compound of claim 2 wherein $R^0$ is hydrogen, —O—($X^1$)$_i$, —$X^0$—O—C(O)—$C_1$–$C_4$ alkyl or —O—$R^3$;

$R^1$ is hydrogen, hydroxy, $C_1$–$C_6$ alkoxy or —O—$R^3$;

$X^0$ is a bond;

$X^1$ is an amino acid ester of glycine, alanine or valine;

i is 1 or 2;

$R^3$ is $C_2$–$C_6$ alkenyl, or —$CH_2$—$R^{3a}$;

$R^{3a}$ is p-fluorophenyl;

$R^4$ is =N—$R^5$;

$R^5$ is hydroxy, or dimethylamino;

$R^6$ is hydrogen, bromo or =O;

$R^7$ is methyl; and $R^8$ is methoxy;

or a pharmaceutically acceptable salt thereof.

4. The compound of claim 3 wherein $R^0$ is hydrogen, —O—$(X^1)_i$, —O—C(O)methyl or —O—$R^3$;

$R^1$ is hydrogen, hydroxy, $C_1$–$C_4$ alkoxy or —O—$R^3$;

$X^1$ is an amino acid ester of glycine, alanine or valine;

$R^4$ is =N—$R^5$;

$R^5$ is hydroxy;

$R^6$ is hydrogen;

or a pharmaceutically acceptable salt thereof.

5. The compound of claim 1 wherein $R^4$ is =N—OH.

6. The compound of claim 2 wherein $R^4$ is =N—OH.

7. The compound of claim 3 wherein $R^4$ is =N—OH.

* * * * *